United States Patent [19]
Watkins et al.

[11] Patent Number: 5,856,189
[45] Date of Patent: Jan. 5, 1999

[54] CELL CULTURE MODEL FOR DRUG BIOAVAILABILITY

[75] Inventors: Paul B. Watkins, Ann Arbor; Phyllissa Schmiedlin-Ren, Brighton, both of Mich.

[73] Assignee: The Regents of the University of Michigan, Ann Arbor, Mich.

[21] Appl. No.: 779,596

[22] Filed: Jan. 7, 1997

[51] Int. Cl.$^6$ .............................. C12N 5/06; C12N 5/08; C12N 1/38
[52] U.S. Cl. ........................... 435/375; 435/366; 435/370; 435/352; 435/384; 435/363
[58] Field of Search ..................................... 435/363, 366, 435/370, 352, 384, 375

[56] References Cited

PUBLICATIONS

Cross, et al., *Naunyn–Schmiedeberg's Arch. Pharmacol.*, vol. 347, pp. 105–110, 1993.
Schmiedlin–Ren, et al., *Molecular Pharmacology*, vol. 51, pp. 741–754, 1997.
Riley, et al., *Biochim. Biophys. Acta,* vol. 1066, No. 2, pp. 175–182, Jul. 1991, Abstract Only.

*Primary Examiner*—Toni R. Scheiner
*Attorney, Agent, or Firm*—Medlen & Carroll, LLP

[57] ABSTRACT

A model utilizing cells for assessing oral bioavailability and potential drug-drug interactions of pharmacological agents is described. The model subjects cells (e.g., Caco-2 cells) to conditions that result in reliable expression of catalytically-active CYP3A4 at levels that appear to be comparable to levels present in mature enterocytes. These conditions include plating of selected clones on an extracellular matrix, exposure to $1\alpha,25\text{-}(OH)_2\text{-}D_3$ for a defined period of time, and the presence of serum in the medium. The model is useful for defining the role of CYP3A4 in limiting the oral bioavailability of many pharmacological agents and in drug-drug interactions involving CYP3A4 substrates that are believed to occur largely at the level of the intestine.

27 Claims, 17 Drawing Sheets

CELL CULTURE MODEL FOR DRUG BIOAVAILABILITY

This invention was made with United States government support awarded by the National Institute of Health (NIH), Grant Nos. GM 38149 and GM 48349.

FIELD OF THE INVENTION

The present invention relates generally to the bioavailability of pharmacologic agents, and more particularly to a model utilizing cells for assessing oral bioavailability and potential drug-drug interactions.

BACKGROUND OF THE INVENTION

A. Absorption and Bioavailability

Absorption refers to the rate and extent by which a pharmacological agent leaves its site of administration and enters the body. Generally speaking, absorption involves the transfer of the pharmacological agent from the site of administration into the blood stream. The route of administration greatly influences the absorption process. For example, because oral administration frequently involves lipid diffusion of the agent across the lining of the gastrointestinal tract, absorption of orally-administered agents is often dependent on the lipid solubility of the agent. By comparison, pharmacological agents administered intravenously bypass the absorption process because they are introduced directly into the vasculature.

The extent to which a pharmacological agent is absorbed frequently does not correlate with the amount of the agent that is able to exert a pharmacological effect. To illustrate, orally administered agents that are absorbed in the gastrointestinal tract pass through the liver prior to reaching the systemic circulation; as a result, those agents that undergo extensive hepatic metabolism (often referred to as "the first-pass effect") will have a much lower effective concentration when they ultimately reach their site of action. In view of the first-pass effect, clinicians are frequently very interested with the parameter of bioavailability, which refers to the extent to which the agent reaches its site of action (or reaches a biological fluid that provides the agent with access to its site of action) [see, e.g., Goodman and Gilman's *The Pharmacological Basis of Therapeutics* (8th edition, L. S. Goodman, A. Gilman, and A. G. Goodman, eds.) Macmillan Publishing Co. Inc., New York, p. 3–18].

B. Drug Biotransformation

Enzyme systems involved in the biotransformation (metabolism) of a large proportion of xenobiotics (including many commonly administered pharmacological agents) are primarily located in the endoplasmic reticulum of the liver (termed "the microsomal fraction"). In addition, these enzyme systems are located to a lesser extent in, among other places, the epithelium of the Gastrointestinal tract. The biotransformation reactions caused by these enzyme systems result in the first-pass effect mentioned above.

Two major types of enzymatic biotransformation reactions take place. The first type of reactions (phase-I reactions) transform a xenobiotic into a more polar metabolite, frequently through an oxidative process. Oxidative biotransformation reactions are generally conducted by a family of enzymes termed cytochromes P450. The second type of reactions (phase-II or conjugation reactions) couple the xenobiotic (or its polar metabolite) with an endogenous substrate (e.g., glucuronate) [see, e.g., Goodman and Gilman's *The Pharmacological Basis of Therapeutics* (8th edition, L. S. Goodman, A. Gilman, and A. G. Goodman, eds.) Macmillan Publishing Co. Inc., New York, p. 3–18].

The major cytochromes P450 that participate in the phase-I biotransformation reactions of xenobiotics can be grouped into three families: i) CYP1, ii) CYP2, and iii) CYP3. Enzymes within the CYP3A subfamily are found in hepatocytes and small intestinal epithelial cells (enterocytes) and are extensively involved in phase-I biotransformation reactions.

CYP3A4 is the principal cytochrome P450 present in human liver [T. Shimada and F. P. Guengerich, Proc. Natl. Acad. Sci. U.S.A. 86:462–465 (1989)] and enterocytes [P. B. Watkins et al., J. Clin. Invest. 80(4):1029–1036 (1987)]. Intestinal CYP3A4 has been implicated in the metabolic elimination of many drugs [F. P. Guengerich, Toxicol. Lett. 70:133–138 (1994)], and first-pass metabolism by the enzyme is believed to contribute to the poor oral bioavailability of some of these drugs [see, e.g., J. C. Kolars et al., Lancet 338:1488–1490 (1991); M. F. Paine et al., Clin. Pharmacol. Ther. 60:14–24 (1996)].

C. In Vitro Models for Studying Oral Bioavailability and Drug Interactions

In vitro studies have previously been performed with the human colon carcinoma cell line Caco-2 [see, e.g., M. Pinto et al., Biol. Cell 47:323–330 (1983)] to study oral bioavailability. When grown as monolayers on permeable supports, Caco-2 cells have proven useful as a model for studying intestinal permeability [I. J. Hidalgo et al., Gastroenterology 96:736–749 (1989)] and several transport functions, including the transport of bile acids, large neutral amino acids, and some drugs [see, e.g., J. Karlsson et al., Br. J. Pharmacol. 110:1009–1016 (1993); D. T. Thwaites et al., Br. J. Pharmacol. 114:981–986 (1995)].

However, the Caco-2 cell line has thus far fallen short as an ideal model for predicting oral bioavailability or studying drug-drug interactions. For example, cultures of the Caco-2 cell line were capable of metabolizing cyclosporin A to one of the major metabolites, but two other metabolites of cyclosporin A were not detected [L.-S. L. Gan et al., Drug Metab. Dispos. 24:344–349 (1996)]. Moreover, the rate of nifedipine oxidation has also been reported to be low in Caco-2 cells [X. Boulenc et al., J. Pharmacol. Exp. Ther. 263:1471–1478 (1992)].

In view of the shortcomings of present models, what is needed is an in vitro model, associated with reproducible results, for accurately predicting bioavailability of pharmacological agents and for studying drug-drug interactions.

SUMMARY OF THE INVENTION

The human colon carcinoma cell line, Caco-2, is widely used as a model for oral absorption and bioavailability of xenobiotics. The usefulness of Caco-2 cells has been limited, however, because they do not express appreciable quantities of CYP3A4, the principle cytochrome P450 present in human small bowel epithelial cells. The present invention discloses that exposure of confluent cells to certain vitamin $D_3$ analogs, specifically $1\alpha,25$-dihydroxyvitamin $D_3$ ($1\alpha,25$-$(OH)_2$-$D_3$), results in a dose-and duration-dependent increase in expression of metabolically-active CYP3A4. While Caco-2 cells are utilized in one embodiment, it should be emphasized that the methods of the present invention are not limited to use with Caco-2 cells. Indeed, the present invention contemplates application of the methods of the present invention to other cell lines representative of the bioavailability of pharmacological agents in humans following oral administration. Such cell lines may include, but are not limited to, intestinal epithelial cells, cell lines derived from enterocytes, and other human colon adenocarcinoma cell lines (e.g., HT-29, SW480, SW116, SW1417, LS180, and LS174T) besides Caco-2. Additionally, the present invention contemplates application of the methods described hereafter to cells or cell lines to model absorption of compounds applied topically (e.g., primary keratinocyte cultures), to cells or cell lines to model renal metabolism (e.g., primary proximal tubule cell cultures, HK-2), and other extrahepatic metabolism (e.g., HS766T) of pharmacologic agents.

More specifically, the present invention discloses that treatment of cells with $1\alpha,25\text{-}(OH)_2\text{-}D_3$, beginning upon confluence, results in a dose- and duration-dependent increase in CYP3A4 mRNA and protein, with little apparent effect on the expression of CYP3A5 or CYP3A7. This treatment also results in increases in NADPH cytochrome P450 reductase and P-glycoprotein (the MDR1 gene product), but has no detectable effect on expression of CYP1A1, CYP2D6, cytochrome $b_5$, liver or intestinal fatty acid binding proteins, or villin. By comparison, while 25-hydroxy vitamin $D_3$ (25-OH-$D_3$) was found to reproduce the effects of $1\alpha,25\text{-}(OH)_2\text{-}D_3$, it was found to be less efficacious than the dihydroxy compound. The present invention also contemplates the use of other analogs of vitamin $D_3$.

As part of the present invention, expression of CYP3A4 is further enhanced when the cells are grown on certain extracellular matrices. Laminin is a preferred extracellular matrix of the present invention. Maximal expression of CYP3A4 requires an extracellular matrix on a permeable support and the presence of serum.

In the treated cells, the intrinsic formation clearance of 1'hydroxymidazolam (a reaction characteristically catalyzed by CYP3A enzymes) was estimated to be only slightly lower than that of human jejunal mucosa. Similarly, the 1'-OH-midazolam/4-OH-midazolam product ratio produced by the cells is comparable to that observed in human jejunal microsomes. Thus, the treated cells of the present invention are representative of xenobiotic metabolism in humans.

More specifically, the present invention contemplates a method of treating cells, comprising the steps of: a) providing: i) cells responsive to treatment with analogs of vitamin $D_3$, ii) an analog of vitamin $D_3$, and iii) an extracellular matrix; b) plating the cells on the extracellular matrix; and c) treating the plated cells with the analog of vitamin $D_3$. In one embodiment, the treating causes the cells to exhibit enhanced expression of CYP3A4.

In a further embodiment, the cells are from a cell line selected from the group consisting of hepatocellular carcinoma cells, colonic adenocarcinoma cells, pancreatic carcinoma cells, pancreatic adenocarcinoma cells, skin cells, and kidney cells. In a still further embodiment, the cells are Caco-2 cells.

In a particular embodiment, the method set forth above further comprises, prior to step b), seeding the cells onto a cell support matrix. In some embodiments, the cell support matrix is a culture insert; the culture insert is permeable in still further embodiments. In additional embodiments, the analog of vitamin $D_3$ is selected from the group consisting of $1\alpha,25$-dihydroxyvitamin $D_3$ and 25-hydroxyvitamin $D_3$. Furthermore, in particular embodiments the extracellular matrix is selected from the group consisting of unpolymerized collagen type I, polymerized collagen type I, collagen type IV, laminin, Matrigel, and Growth Factor Reduced Matrigel. Finally, in some embodiments of the method, the cells are grown in the presence of serum.

The present invention also contemplates a cell line with enhanced expression of a member of the CYP3A subfamily made by the process of: a) providing: i) Caco-2 cells, ii) an analog of vitamin $D_3$, and iii) an extracellular matrix; b) plating the Caco-2 cells on the extracellular matrix; c) treating the plated Caco-2 cells with the analog of vitamin $D_3$; and d) isolating those treated cells that exhibit enhanced expression of a member of the CYP3A subfamily. In one embodiment, the member comprises CYP3A4.

In particular embodiments, the cell line further comprises, prior to step b), seeding the Caco-2 cells onto a cell support matrix. In some embodiments, the cell support matrix is a culture insert; when the cell support matrix is a culture insert, it is permeable in certain embodiments.

In some embodiments of the cell line, the analog of vitamin $D_3$ is selected from the group consisting of $1\alpha,25$-dihydroxyvitamin $D_3$ and 25-hydroxyvitamin $D_3$. Moreover, in certain embodiments, the extracellular matrix is selected from the group consisting of unpolymerized collagen type I, polymerized collagen type I, collagen type IV, laminin, Matrigel, and Growth Factor Reduced Matrigel.

In further embodiments of the cell line, the treating comprises exposing the Caco-2 cells to the vitamin $D_3$ analog for approximately two weeks beginning at the time of confluence. In still further embodiments, the Caco-2 cells are grown in the presence of serum.

Furthermore, the present invention contemplates a system for screening the bioavailability of compounds, comprising gastrointestinally-derived cells exhibiting enhanced expression of CYP3A4 seeded onto a cell support matrix. In certain embodiments, the cell support matrix is a culture insert; the culture insert is permeable in some embodiments.

In particular embodiments, the enhanced expression by the cells results from exposing the cells to an analog of vitamin $D_3$. In some embodiments, the analog of vitamin $D_3$ is selected from the group consisting of $1\alpha,25$-dihydroxyvitamin $D_3$ and 25-hydroxyvitamin $D_3$. In other embodiments, the cells are grown in the presence of serum.

Finally, in some embodiments of the system, the gastrointestinally-derived cells are from a cell line selected from the group consisting of colonic adenocarcinoma cells, stomach adenocarcinoma cells, and stomach carcinoma cells. In particular embodiments, the colonic adenocarcinoma cells are Caco-2 cells.

DEFINITIONS

Figure 1:
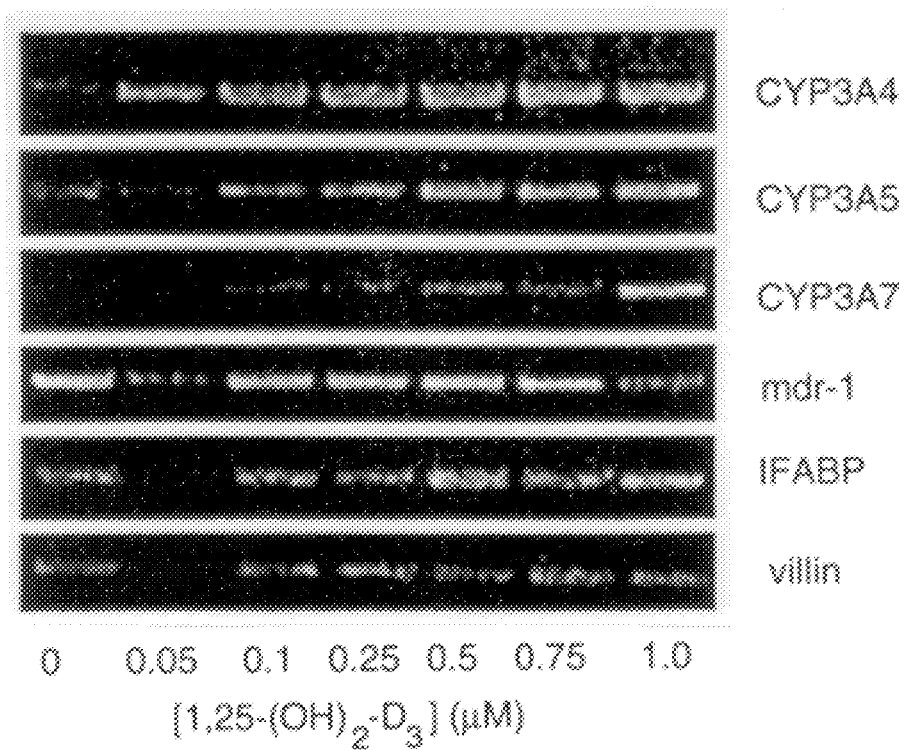
FIG. 1 is an ethidium bromide stained agarose gel indicating the changes in Caco-2 cell levels of specific mRNAs in response to treatment with varying doses of $1\alpha,25\text{-}(OH)_2\text{-}D_3$.

To facilitate understanding of the present invention, a number of terms are defined below.

The term "Caco-2 cells" refers to cells derived from the human colon adenocarcinoma cell line given the ATCC Assession number HTB37.

The terms "gastrointestinally-derived cells," "gastoenterically-derived cells," and the like refer to cells derived from tissue from the stomach, the small intestine (comprising the duodenum, jejunum, and ileum), and the large intestine (comprising the cecum, colon, rectum, and anal canal).

The term "carcinoma" refers broadly to any of the various types of malignant neoplasms derived from epithelial tissue in numerous sites, including the stomach and intestines. The term "adenocarcinoma" refers broadly to a malignant neoplasm of epithelial cells in a glandular or gland-like pattern; examples include, but are not limited to, renal adenocarcinoma and papillary adenocarcinoma.

The phrase "screening the bioavailability of compounds" refers to the process of introducing compounds into a cell culture model that has effects representative of the first-pass effect observed in human subjects. In other words, the cell culture model provides information regarding the extent to which the compound will reach its site of action following oral administration in humans. It is contemplated that a large number of compounds can be tested using the cell culture model of the present invention; those compounds with favorable bioavailability characteristics (e.g., an effective amount of the compound reproducibly enters the systemic circulation) may then be evaluated further.

The term "analog of vitamin $D_3$" refers to compounds derived from vitamin $D_3$ (cholecalciferol), including, but not limited to, 25-hydroxyvitamin $D_3$ (calcifediol) and $1\alpha,25$-dihydroxyvitamin $D_3$ (calcitriol). The present invention also contemplates that the term "analog of vitamin $D_3$" encompass other compounds derived from vitamin $D_3$; such compounds may be produced, for example, by the addition of alkly, alkoxy, hydroxyl groups, etc. to vitamin $D_3$ to produce compounds that function in a manner similar (e.g., contribute to enhanced catalytic activity) to $1\alpha,25$-dihydroxyvitamin $D_3$ and 25-hydroxyvitamin $D_3$.

The terms "cell support matrix," "cell support matrices," and the like refer broadly to the foundation onto which cells from isolated clones may be seeded to allow for growth and further treatment (e.g., the application of vitamin $D_3$ analogs). The present invention is not limited to the use of any particular cell support matrix. Cell support matrices contemplated for use with the present invention include, but are not limited to, solid supports such as microcarrier beads and culture plate inserts.

The terms "culture insert," "culture plate inserts," and the like refer to the cell support matrices which generally comprise a membrane that supports cell growth. The present invention is not limited to any particular type of culture insert; inserts comprised of polyethylene terephthalate, polycarbonate, teflon, and mixed cellulose esters, among others, may be used in conjunction with the present invention. Culture inserts are commercially available from a number of manufacturers, including Collaborative Biomedical Products, Costar, ICN, and Millipore. In particular embodiments, the culture inserts used in conjunction with the present invention comprise a permeable microporous membrane that allows free diffusion of ions and macromolecules; as a result, cells grown on such inserts generally mimic the in vivo situation more closely than cells grown on plastic plates. However, the present invention does not require the use of permeable supports.

The term "extracellular matrix" refers broadly to material for supporting cell growth. It is not intended that the present invention be limited by the particular material; the present invention contemplates a wide variety of materials, including, but not limited to, material that is distributed throughout the body of multicellular organisms such as glycoproteins, proteoglycans, and complex carbohydrates. The present invention contemplates the use of a substratum of extracellular matrix with the culture inserts on which the cells (e.g., Caco-2 cells) are plated. Although the present invention is not limited by the nature of the extracellular matrix, the preferred extracellular matrices include Matrigel, Growth Factor Reduced Matrigel, fibrillar collagen, laminin, fibronectin, and collagen type IV. Laminin is the most preferred extracellular matrix for use with the present invention. However, the present invention is not limited to the use of purified laminin, nor to the use of culture inserts that are commercially coated with laminin or other extracellular matrices.

The term "approximately two weeks" preferably refers to the period from ten days to eighteen days and most preferably from thirteen days to fifteen days.

The phrase "beginning at the time of confluence" refers to that time when there is a growing together of cells so as to form a merged mass (e.g., a confluent lawn of cells). The achievement of confluence can be determined, for example, by measuring transepithelial resistance using a Millicell™ ERS device.

The term "serum" refers broadly to sera derived from both human and animal sources. Animal sera contemplated for use with the present invention include, but are not limited to, bovine (such as fetal bovine serum or "FBS"), chicken, equine, or porcine sera. In a preferred embodiment, cells are grown in 5% FBS.

As previously alluded to, the major cytochromes P450 that participate in the phase-I biotransformation reactions of xenobiotics can be grouped into three families: i) CYP1, ii) CYP2, and iii) CYP3. Enzymes within the CYP3A subfamily are found in hepatocytes and enterocytes and are extensively involved in phase-I biotransformation reactions. The phrase "enhanced expression of a member of the CYP3A subfamily" refers to enhanced expression of, among other isoforms CYP3A4, CYP3A5, and CYP3A7. Generally speaking, CYP3A4 is the predominant CYP3A isoform upregulated by the conditions of the present invention.

The phrase "cells responsive to treatment with an analog of vitamin $D_3$" and the like refer to cell lines that exhibit enhanced expression of CYP3A catalytic activity following treatment with an analog of vitamin $D_3$. The comprehensive screening procedure set forth in Table 1 can be used to evaluate those cells (such as the cell lines presented below in Table 2) that may be useful for screening the bioavailability of compounds. The colonic adenocarcinoma cell lines (see Table 2) are especially contemplated for use with the screening procedure. Reference to a particular example is given with each determination; the indicated examples provide a detailed description of how the determination is to be carried out.

Moreover, because drug interactions involving induction or inhibition of CYP3A4 may be largely occurring at the level of the intestine (and not exclusively within the liver as originally thought) [see, e.g., J. C. Kolars et al., J. Clin. Invest. 90(5):1971–78 (1992)], an in vitro model suitable for studying the role of intestinal CYP3A4 in drug-drug interactions is also advantageous.

Currently used Caco-2 cell lines fail to express appreciable quantities of CYP3A4, the principle cytochrome P450 present in human small bowel epithelial cells. The present invention overcomes this limitation by providing methods for treating Caco-2 cells to enhance expression of catalytically-active CYP3A4. However, the methods of the present invention are not limited to use with Caco-2 cells. Indeed, the present invention contemplates application of the methods to other cell lines. Such cell lines may include, but are not limited to, intestinal epithelial cells, cell lines derived from enterocytes, pancreatic cells or cell lines (e.g., HS766T), kidney cells or cell lines (e.g., HK-2), skin cells (keratinocytes) or cell lines and other human colon adenocarcinoma cell lines (e.g., HT-29, SW116, and LS174T) besides Caco-2. Table 2 summarizes some of the cell lines contemplated for use with the present invention; of course, the present invention may be practiced with cell types other than those set forth in Table 2.

TABLE 2

| Cell Line | Origin | ATCC Number |
|---|---|---|
| HT-29 | colonic adenocarcinoma | HTB 38 |
| LS180 | colonic adenocarcinoma | CL 187 |
| LS 174T | colonic adenocarcinoma | CL 188 |
| SW480 | colonic adenocarcinoma | CCL 228 |
| SW1116 | colonic adenocarcinoma | CCL 233 |
| SW1417 | colonic adenocarcinoma | CCL 238 |
| Hs 766T | pancreatic carcinoma | HTB 134 |

TABLE 1

| Step | Determination | Conclusion |
|---|---|---|
| I | Grow cells on PET culture inserts commercially plated with an extracellular matrix (e.g. . . . , laminin). (see, e.g., Example 2). | Proceed to Step II with cells demonstrating favorable growth characteristics |
| II | Determine in vitro the dose-response effect of various treatment regimens of a vitamin $D_3$ analog (e.g., 1α, 25-dihdroxyvitamin $D_3$). (see, e.g., Example 3). | Proceed To Step III with those cells that increase CYP3A expression |
| III | Determine the effect that duration of exposure of treatment with vitamin $D_3$ analogs has on protein expression. (see, e.g, Example 7). | Utilize cells derived from Step III in a model for screening the bioavailability of compounds |

As illustrated by this outline of the sequence of experimental procedures and the description of the procedures themselves, thoughtful consideration allows any cell line (e.g., "Cell Line X") to be evaluated for use with the present invention. Moreover, the present invention also contemplates the use of primary cultures of cells derived from, for example, intestinal cells.

DESCRIPTION OF THE INVENTION

The present invention relates generally to the bioavailability of pharmacologic agents, and more particularly to a model utilizing cells for assessing oral bioavailability and potential drug-drug interactions. Specifically, the present invention involves a model utilizing treated cells (e.g., Caco-2 cells) for defining the role of CYP3A4 in limiting the oral bioavailability of many pharmacological agents.

TABLE 2-continued

| Cell Line | Origin | ATCC Number |
|---|---|---|
| HPAC | pancreatic adenocarcinoma | CRL 2119 |
| HPAF II | pancreatic adenocarcinoma | CRL 1997 |
| AGS | stomach adenocarcinoma | CRL 1739 |
| Hs 746T | stomach carcinoma | HTB 135 |
| Hep G2 | hepatocellular cacinoma | HB 8065 |
| HK-2 | kidney (immortalized cell line) | CRL 2190 |

Following treatment with the methods described hereafter, the cell lines contemplated for use with the present invention may be used, for example, as models of the bioavailability of pharmacological agents in humans.

The present invention describes three major conditions under which cells reliably express catalytically-active CYP3A4 at levels that appear to be comparable to levels present in mature enterocytes: i) an extracellular matrix, generally on a permeable support with low non-specific binding properties, ii) exposure to $1\alpha,25$-$(OH)_2$-$D_3$ for a defined period of time (e.g. two weeks) beginning at the time of confluence, and iii) serum. It is preferred, though not required, that each of the three conditions be present simultaneously. In a preferred embodiment, clones are made as described below, those clones that exhibit favorable growth characteristics are selected, the selected clones are grown on, e.g., laminin-coated inserts and treated with $1\alpha,25$-$(OH)_2$-$D_3$, and finally the clones are screened for maximum CYP3A4 expression.

I. GROWTH OF SELECT CLONES ON CULTURE INSERTS

A. Isolation of Clones

In one embodiment, the present invention first involves the isolation of Caco-2 clones which exhibit favorable growth characteristics. Thereafter, the Caco-2 cells are subjected to a two-part protocol that results in expression of metabolically active CYP3A4 to levels comparable to those present in small intestinal enterocytes. As described in detail below, the first step involves plating the cells on an extracellular matrix, and the second step involves adding a vitamin $D_3$ analog to the medium.

Initially, genetic homogeneity is obtained among Caco-2 cells by limiting dilution. The present invention is not limited to the use of this technique; rather, any technique that results in apparent genetic homogeneity is contemplated for use with the present invention. When clones which exhibit favorable growth characteristics are subjected to the two-part culture protocol, the Caco-2 clone (or clones) that exhibit high levels of CYP3A4 expression may then be chosen for use in the model of the present invention. As set forth in detail in the Experimental section, the present inventors isolated one particular clone ("clone #7") that possessed both high levels of CYP3A4 expression and favorable growth characteristics.

It should be noted that the stability of the clones with respect to CYP3A4 expression is unknown since cells of relatively low passage numbers have only been used thus far. However, while a particular clone (e.g., clone #7) may be associated with favorable growth characteristics and high levels of CYP3A4 expression, the use of that particular clone is not critical to obtaining measurable CYP3A4 catalytic activity. Therefore, clonal instability is not a major consideration so long as it is monitored.

Of note, Caco-2 cells have previously been transfected with a vector that caused the expression of CYP3A4. The cells were found to form monolayers and deemed suitable for drug studies [C. L. Crespi et al., Abstract P-7, XIth International Symposium on Microsomes and Drug Oxidations: Final Program and Abstracts, University of California at Los Angeles, Jul. 21–24, 1996]. While these cells may result in relatively high expression of CYP3A4, they are associated with several shortcomings that make them less than ideal as a model for drug screening. For example, the catalytic activity of the cells is nominal compared to the treated cells of the present invention. Moreover, the extra-chromosomal vector is not passed from one cell generation to the next, thereby limiting the useful life of the cells.

B. Seeding Cells Onto Culture Inserts

In preferred embodiments, cells from the isolated clones are seeded onto cell support matrices. The present invention is not limited to the use of any particular cell support matrix. Cell support matrices contemplated for use with the present invention include, but are not limited to, microcarrier beads and culture plate inserts that are commercially available (e.g., Collaborative Biomedical Products, Costar, ICN and Millipore).

Culture inserts are utilized in preferred embodiments of the present invention. Culture inserts offer several advantages over standard plastic plates. For example, inserts comprising a microporous membrane allow free diffusion of ions and macromolecules; as a result, cells grown on such inserts generally mimic the in vivo situation more closely than cells grown on plastic plates. The present invention is not limited to any particular type of culture insert; inserts comprised of polyethylene terephthalate, polycarbonate, teflon, and mixed cellulose esters, among others, may be used in conjunction with the present invention. Though the experiments of the present invention were all performed in conjunction with permeable supports, the present invention does not require the use of such supports.

One preferred culture insert is a polyethylene terephthalate (PET) insert (Colloborative Biomedical Products) that is transparent and exhibits low protein binding. This insert can be purchased pre-coated with laminin or uncoated for subsequent application of matrix. Another preferred culture insert is the Millicell™ CM insert (Millipore). This insert includes a transparent, low-protein binding membrane that allows growing cells to be viewed by light microscopy. In addition, the surface of the Millicell™ CM insert can be modified by the application of cell matrix coatings like laminin and collagen which enhance the growth of attachment-dependent cells. As set forth in the Experimental section, Millicell™ CM culture inserts were primarily used in the experiments of the present invention.

Caco-2 cells grown on uncoated permeable supports, as compared to those grown on plastic, have been reported to express apolipoproteins in a pattern more closely resembling adult human enterocytes [R. D. Wagner et at., Am. J. Physiol. 263(2Pt1):E374-E382 (1992)]. Thus, growth on a permeable support, even in the absence of an extracellular matrix, seems to result in a more differentiated phenotype in at least some respects.

II. GROWTH OF CELLS ON AN EXTRACELLULAR MATRIX

Maximal expression of CYP3A4 levels in cells (e.g., the Caco-2 cells contemplated in one embodiment) of the present invention occurs when the cells are plated on an extracellular matrix. The extracellular matrix is the non-cellular material distributed throughout the body of multi-cellular organisms. It is comprised of a number of different types of molecules, including glycoproteins, proteoglycans, and complex carbohydrates.

Some of the main functions of the extracellular matrix involve the provision of a substrate and pathways for cell adhesion and migration and the regulation of cellular differentiation and metabolic function. Indeed, the role of extracellular matrix in enhancing cellular differentiation and gene expression in cultured cells has been reported [J. C. Adams and F. M. Watt, Development 117:1183–1198 (1993)]. In addition, it is known that extracellular matrix proteins (especially laminin) increase the expression of brush border hydrolases in Caco-2 cells [M. D. Basson et al., Exp. Cell Res. 225:301–305 (1996)].

The present invention contemplates the use of a substratum of extracellular matrix with the culture inserts on which the cells are plated. Although the present invention is not limited by the nature of the extracellular matrix, the preferred extracellular matrices include Matrigel, Growth Factor Reduced Matrigel, fibrillar collagen, laminin, and collagen type IV.

Use of a substratum of Matrigel has been shown to improve inducibility of CYP3A in cultured rat hepatocytes [E. G. Schuetz et al., J. Cell. Physiol. 134:309–323 (1988)]. Laminin, the chief matrix component of Matrigel, is known to promote differentiation of fetal enterocytes as assessed by cellular polarization and expression of alkaline phosphatase [U. Hahn, Scand. J. Gastroenterol. Suppl.151:70–78 (1988) ]. As described in detail in the Experimental section, through the use of culture inserts commercially coated with laminin, the Caco-2 cells readily formed a monolayer covering the entire surface of the membrane, and, when treated with $1\alpha,25\text{-}(OH)_2\text{-}D_3$, expressed catalytically active CYP3A4 in levels equivalent to that of $1\alpha,25\text{-}(OH)_2\text{-}D_3$-treated Caco-2 cells grown on Matrigel.

Laminin is the most preferred extracellular matrix for use with the present invention. However, the present invention is not limited to the use of laminin, nor to the use of culture inserts that are commercially coated with that or other extracellular matrices. Unlike Matrigel and Growth Factor Reduced Matrigel, laminin is a single component "defined" matrix and is associated with a more consistent monolayer pattern of growth by Caco-2 cells in culture than Matrigel and Growth Factor Reduced Matrigel. Furthermore, at the coating density used in the experiments described below, the Growth Factor Reduced matrix formed a 1–2 mm thick gel which would be expected to interfere with diffusion and confound volume of distribution calculations in planned applications of this culture model. Of course, other cells may exhibit different growth characteristics, and other growth conditions are contemplated by the present invention.

Figure 8A:
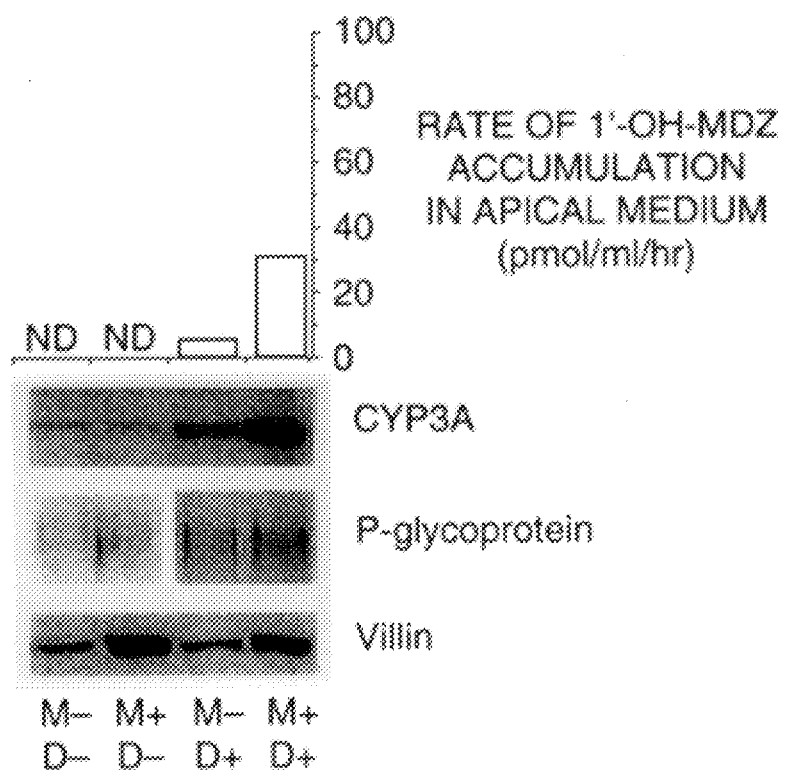
FIG. 8A is a comparison of CYP3A catalytic activity (top panel) and CYP3A expression (immunoblots in bottom panel) in the presence and absence of Matrigel and treatment with $1\alpha,25\text{-(OH)}_2\text{-}D_3$.

While the presence of an extracellular matrix did not itself result in increased expression of CYP3A4, it was essential in achieving the maximal increase in CYP3A4 expression in response to $1\alpha,25\text{-}(OH)_2\text{-}D_3$ (see FIG. 8A). Though an understanding of the mechanism by which $1\alpha,25\text{-}(OH)_2\text{-}D_3$ exerts this effect is not required in order to practice the present invention, it is possible that the extracellular matrix induces increased expression of the vitamin D receptor, thereby increasing vitamin D responsiveness. Treatment of cells with vitamin $D_3$ analogs is described hereafter.

III. EXPOSURE OF CELLS TO VITAMIN $D_3$ ANALOGS

The present invention contemplates the treatment of cells plated on an extracellular matrix with an analog of Vitamin $D_3$; the cells are Caco-2 cells in one embodiment. In preferred embodiments, the cells are treated with either $25\text{-}(OH)\text{-}D_3$ or $1\alpha,25\text{-}(OH)_2\text{-}D_3$, while the most preferred embodiment involves treatment with $1\alpha,25\text{-}(OH)_2\text{-}D_3$. The treated cells form polarized monolayers and express high levels of catalytically active CYP3A4. As set forth above, it is contemplated that such cells can be used to screen candidate drugs during development to see how readily the parent compound will gain access into the body when given orally.

The literature contains reports of exposure of Caco-2 cells to vitamin $D_3$. For example, Giuliano et al. [Arch. Biochem. BioPhys. (1991)] notes that vitamin $D_3$ led to a decrease in cell growth. In addition, Halline et al. [Endocrinology 134:1710–1717 (1994)] indicate that vitamin $D_3$ results in a dose-dependent inhibition of cell proliferation and enhancement and alteration of functional aspects in Caco-2 cells. However, these references do not include a discussion regarding plating the Caco-2 cells on a particular matrix, nor is there a discussion concerning CYP3A4. Indeed, the finding in the present invention that exposure of particular Caco-2 clones, plated on extracellular matrix, to particular Vitamin $D_3$ analogs (especially $1\alpha,25\text{-}(OH)_2\text{-}D_3$) led to a dramatic increase in CYP3A4 expression was unexpected.

Figure 5A:
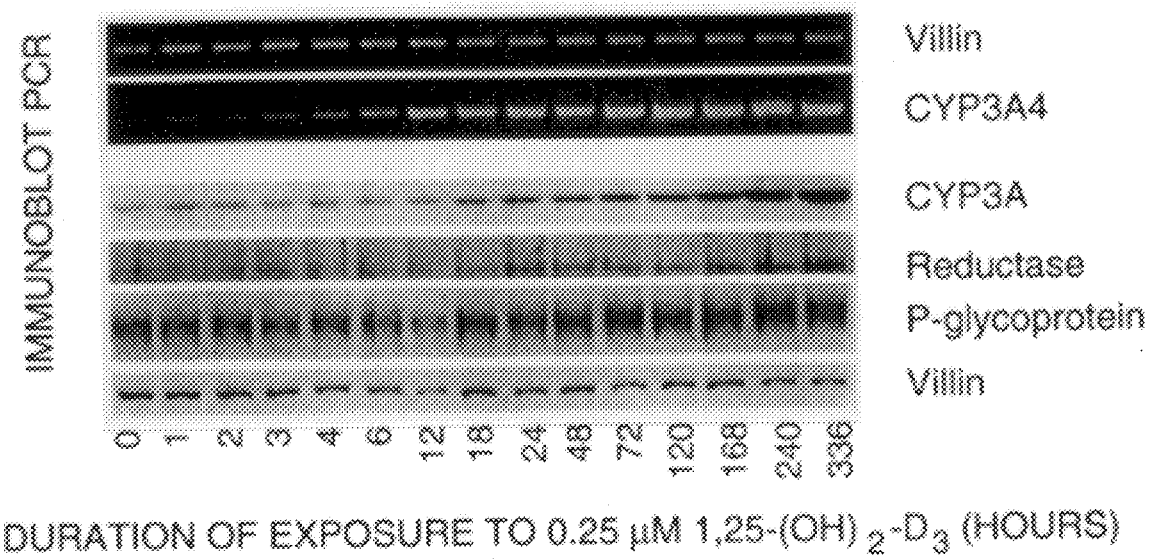
FIG. 5A depicts an ethidium bromide stained agarose gel (top panel labeled "PCR") and an immunoblot (bottom panel labeled "Immunoblot") indicating the duration of exposure to $1\alpha,25\text{-(OH)}_2\text{-}D_3$ necessary to achieve increased expression of CYP3A4 mRNA, CYP3A4, NADPH cytochrome P450 reductase, and P-glycoprotein immunoreactive proteins.

Though the practice of the present invention does not require an understanding of the mechanisms by which the vitamin $D_3$ analogs contribute to the enhancement of the expression of CYP3A4, it appears that the mechanisms involve binding to the vitamin D receptor. Many of the actions of $1\alpha,25\text{-}(OH)_2\text{-}D_3$ [M. W. Walters, Endocr. Rev. 13:719–764 (1992); and Z. W. Norman et al., J. Steroid Biochem. Molec. Biol. 41:231–240 (1992)] are mediated by the binding of $1\alpha,25\text{-}(OH)_2\text{-}D_3$ to an intracellular vitamin D receptor known to be present in Caco-2 cells [A. R. Giuliano et al, Arch. Biochem. Biophys. 285:261–269 (1991)]. The intracellular vitamin D receptor is thereby enabled to bind to vitamin D-responsive elements in various genes, resulting in their up- or down-regulation. The relative responsiveness of CYP3A4 expression in the Caco-2 cells to $1\alpha,25\text{-}(OH)_2\text{-}D_3$, or unhydroxylated vitamin $D_3$ or $D_2$ correlates with the relative binding affinities of these compounds to the vitamin D receptor. In addition, the time between initiation of treatment with $1\alpha,25\text{-}(OH)_2\text{-}D_3$ and detectable increase in CYP3A4 mRNA (approximately 3–4 h; FIG. 5A) is consistent with transcriptional activation. These findings make it likely that the effects of vitamin D on CYP3A4 expression are mediated through ligand interactions with the receptor. It should be noted that if the effects of vitamin D on CYP3A4 expression are mediated through ligand interactions with the vitamin D receptor, the vitamin D receptor might be transfected into cells that have little or no expression of the receptor; in this way, cells that are initially unresponsive to vitamin D would exhibit CYP3A4 catalytic activity.

It should be noted that, in response to the methods of the present invention, the catalytic activity of CYP3A4 rose far greater than the increase in aggregate CYP3A immunoreactive protein. In other words, one effect of the present invention is to "functionalize" cytochromes P450, creating more catalytic activity per molecule of enzyme. Though a precise understanding of the mechanism underlying this effect is not required to practice the present invention, the effect may be due to, among other mechanisms, increased incorporation of the prosthetic heme group into the enzyme protein, improved linking between the enzyme and its coenzyme NADPH cytochrome P450 reductase, or better orientation of the proteins in the endoplasmic reticulum. The methods of the present invention may be useful in improving the catalytic activity of other enzymes present in the cells.

IV. SERUM

In a preferred embodiment, the cells of the present invention are grown in a medium containing serum. As described in detail in the Experimental section, the presence of 5% FBS in the medium was found to be required for a maximal increase in CYP3A4 expression in Caco-2 cells in response to $1\alpha,25\text{-}(OH)_2\text{-}D_3(0.25\ \mu M)$. Indeed, the presence of 5% FBS resulted in demonstrably increased expression of CYP3A and catalytic activity (see FIG. 8C). The results also indicated that P-glycoprotein expression required the presence of 5% FBS for a complete response to $1\alpha,25\text{-}(OH)_2\text{-}D_3$, although the magnitude of the difference between serum-free and 5% FBS cultures was not as great with P-glycoprotein expression as with CYP3A4 expression. Of course, the present invention also contemplates the use of other types of serum (e.g., chicken, human, equine, or porcine sera) and other concentrations of FBS.

Though an understanding of the mechanism of the increased expression of these proteins is not required in order to practice the present invention, 10% serum (following 3 days of serum-free conditions) has been reported to increase vitamin D receptor levels in cultured mouse fibroblast and human breast cancer cell lines [A. V.

Krishnan and D. Feldman, J. Bone Miner. Res. 6:1099–1107 (1991)], and it is possible that a similar effect was produced in the cultures of the present invention. Of note, glucocorticoids, which have been shown to increase the number of vitamin D receptors in rat intestine and in osteoblast-like cells, are unlikely to be a key ingredient in FBS since the addition of 100 nM dexamethasone to the serum free medium did not restore full responsiveness (see Experimental section).

It should be noted that the present invention also contemplates performing drug metabolism studies in a serum-free media. Since drugs vary in their degree of protein binding, it would be desirable to be able to eliminate serum from the medium and manipulate the concentration of albumin or other proteins in a model to study the oral bioavailability of drugs. Elimination of serum from the system would also make it more defined and reproducible.

The present invention contemplates performing drug metabolism studies under serum-free conditions by withdrawing serum for a limited (e.g., 6–24 h) study period following maximization of CYP3A4 expression by a two week treatment with $1\alpha,25\text{-}(OH)_2\text{-}D_3$ or $25\text{-}(OH)\text{-}D_3$. The Experimental section describes a study performed under serum-free conditions.

V. ENHANCED PROTEIN EXPRESSION

A. CYP3A4 is the Predominant CYP3A Isoform

As described in more detail in the Experimental section, the results of the present invention indicate that CYP3A4 is the predominant CYP3A isoform upregulated by the conditions of the present invention. Initially, CYP3A4 mRNA demonstrated the most marked increase in response to $1\alpha,25\text{-}(OH)_2\text{-}D_3$ (see FIG. 1). While there also appeared to While there also appeared to be some increase in the expression of CYP3A5 and CYP3A7 mRNAs, the immunoblots clearly demonstrated that CYP3A5, which was present in untreated Caco-2 cells, was not substantially increased (see FIGS. 3 and 7).

Because CYP3A7-specific antibody is not available, it was not possible to directly assess levels of this protein. However, the midazolam metabolite measurements described in the Experimental section indicate that the Caco-2 cells of the present invention may contain catalytically-active CYP3A7. In incubations with midazolam, CYP3A7 has been reported to generate more 4-OH-MDZ than 1'-OH-MDZ [J. C. Gorski et al., Biochem Pharmacol. 47:1643–1653 (1994)], resulting in a 1'-OH-MDZ/4-OH-MDZ product ratio that is less than unity. The ratios observed by the present inventors (in the range of 5) were lower than would be anticipated from the presence of CYP3A4 and CYP3A5 alone (see Table 7), and could be explained by the presence of relatively small amounts of CYP3A7. The increase in the product ratio from 3.8 in the cells treated with $1\alpha,25\text{-}(OH)_2\text{-}D_3$ for 12 hours to a product ratio greater than 5 with prolonged ($\geq 120$ hours) treatment suggests that CYP3A7 comprised a smaller proportion of the total CYP3A present in treated as compared to untreated cells.

Therefore, in one embodiment, the treated Caco-2 cells of the present invention represent a model that can be utilized for defining the role of CYP3A4 in limiting the oral bioavailability of many pharmacological agents. Moreover, this model can also be used to assess the role of CYP3A4 in drug-drug interactions involving CYP3A4 substrates that are believed to occur largely at the level of the intestine.

B. Enhanced Expression of Other Proteins

While CYP3A4 is the protein whose expression is predominantly enhanced, the culture system of the present invention is associated with increased levels of other proteins as well. As indicated above, the level of CYP3A7 increased somewhat under the culture conditions of the present invention, and levels of NADPH cytochrome P450 reductase and P-glycoprotein also increased (see Experimental section). In addition, the present inventors found immunoreactive CYP1A1 protein to be detectable in uninduced Caco-2 cells; in contrast, others have found CYP1A1 expression by Caco-2 cells (grown on plastic) to require treatment with inducers [T. Prueksaritanont et al., Drug Metab. Dispos. 24:634–642 (1996)]. Similarly, CYP2D6 immunoreactive protein expression also appeared improved over that reported by others in Caco-2 cells [T. Prueksaritanont et al., Drug Metab. Dispos. 24:634–642 (1996)]. Finally, IFABP mRNA and immunoreactive protein were also readily detected in the Caco-2 cells of the present invention. In contrast, other researchers have been unable to detect either IFABP mRNA by Northern blotting or IFABP immunoreactive protein in Caco-2 cells [see, e.g., M. S. Levin et al., J. Lipid Res. 33:9–19 (1992)].

Though an understanding of the mechanism of the increased expression of these proteins is not required in order to practice the present invention, it is believed that the expression of CYP1A1, CYP2D6, and IFABP resulted from the culture conditions rather than genetic differences among Caco-2 cells. This belief is supported by the finding that the expression of these proteins was comparable in all of the clones tested as well as in the parent cell line (see Experimental section). It should be noted that the presence of a permeable support and/or an extracellular matrix may have been responsible for the increased levels of these proteins because their expression was not clearly influenced by $1\alpha,25\text{-}(OH)_2\text{-}D_3$. Thus, the model of the present invention may also be useful, for example, to assess bioavailability of compounds that are affected by these proteins.

VI. SCREENING OF COMPOUNDS

As alluded to above, the treated cells of the present invention represent a useful in vitro model for determining the apparent bioavailability of orally administered candidate compounds. In one embodiment, the methods of the present invention are applied to Caco-2 cells. More specifically, the present invention provides a model for defining the role of CYP3A4 in limiting the oral bioavailability of many pharmacological agents and in drug-drug interactions involving CYP3A4 substrates that are believed to occur largely at the level of the intestine. This section summarizes one method of how the treated cells of the present invention may be used to assess bioavailability; of course, other procedures known to those skilled in the art can also be used with the model of the present invention.

A compound being tested will be formulated into a pharmacologically acceptable solution (i.e., a solution that does not adversely affect the stability of the compound) that contains concentrations of the compound similar to that expected following oral administration of a therapeutic amount of the compound in humans. In some embodiments, the compound being tested contains a radiolabelled marker (e.g $^3H$, $^{14}C$, and $^{15}N_3$). The compound will be administered to the apical side of monolayers of treated cells, as described in the Experimental section in relation to Caco-2 cells. At regular intervals, samples will be withdrawn from the basal side, and analyzed for parent drug and metabolites. Comparison of the amount of compound measured on the basal side versus the amount of compound introduced onto the apical side will provide an estimate of bioavailability. Of course, other mechanisms of estimating bioavailability utilizing the cells and the methods described are also contemplated for use with the present invention.

The present invention is not limited to screening any particular compounds or group of compounds. However, it is anticipated that the model of the present invention will be especially useful in testing compounds that are related to known compounds which undergo extensive first-pass metabolism (e.g, midazolam). It is anticipated that known compounds will be tested first because researchers are already familiar with many of the effects of these compounds on humans. Although the in vitro testing will need to be supplemented and confirmed by testing in human subjects, the model of the present invention will allow a large number of compounds to be screened at an early stage of drug development.

The in vitro model of the present invention represents a major advance in the study of the role of intestinal CYP3A4 in determining oral bioavailability and in drug-drug interactions. The in vitro model entails a system that is useful in the screening of compounds for utility as potential pharmacological agents.

EXPERIMENTAL

In the experimental disclosure which follows, the following abbreviations apply: M (Molar); mM (millimolar); $\mu$M (micromolar); N (Normal); mol (moles); mmol (millimoles); $\mu$mol (micromoles); nmol (nanomoles); pmol (picomoles); g (grams); mg (milligrams); $\mu$g (micrograms); L (liters); mL (milliliters); $\mu$L (microliters); cm (centimeters); mm (millimeters); $\mu$m (micrometers); nm (nanometers); min. (minutes); s and sec. (seconds); °C. (degrees Centigrade); bp (base pairs); BSA (bovine serum albumin); BSS (Balanced Salt Solution); CYP (cytochrome P450); $D_3$ (vitamin $D_3$); 1$\alpha$,25-(OH)$_2$-$D_3$ (1$\alpha$,25-dihydroxyvitamin $D_3$); 25-OH-$D_3$ (25-hydroxyvitamin $D_3$); DEPC (diethyl pyrocarbonate); DMEM (Dulbecco's Modified Eagle Medium); ECL (enhanced chemiluminescence); EDTA (ethylenediaminetetraacetic acid); FBS (fetal bovine serum); H&E (hematoxylin and eosin); HEPES (N-(2-hydroxyethyl) piperazine-N'-(2-ethanesulfonic acid)); IFABP (intestinal fatty acid binding protein); LFABP (liver fatty acid binding protein); mdr-1 (multidrug resistance gene); MDZ (midazolam); 1'-OH-MDZ (1'-hydroxymidazolam); 4-OH-MDZ (4-hydroxymidazolam); ND (not done); PCR (polymerase chain reaction); PET (polyethylene terephthalate); PMSF (phenylmethylsulfonyl fluoride); RT-PCR (reverse transcription-polymerase chain reaction); SDS (sodium dodecyl sulfate); tris (tris(hydroxymethyl) aminomethane); v/v (volume/volume); Amersham (Amersham Corp., Arlington Heights, Ill.; Applied Biosystems (Norwalk, Conn.); Apple (Apple Computers, Cupertino, Calif.); ATCC (American Type Culture Collection; Rockville, Md.); Calbiochem (La Jolla, Calif.); Chemicon (Chemicon International, Temecula, Calif.); Collaborative Biomedical Products (Bedford, Mass.); Eli Lilly (Indianapolis, Ind.); Gentest (Gentest Corp., Woburn, Mass.); Gibco BRL (Grand Island, N.Y.); Hewlett-Packard (Palo Alto, Calif.); Hyclone (Logan, Utah); ICN (ICN Biomedicals, Inc., Costa Mesa, Calif.); Invitrogen (San Diego, Calif.); Millipore (Millipore Corporation, Bedford, Mass.; Oncogene (Oncogene Science, Uniondale, N.Y.); Pierce Chemical (Rockford, Ill.); Roche (Roche Laboratories, Nutley, N.J.); Seikagaku America (St. Petersburg, Fla.); Sigma (Sigma Chemical Co., St. Louis, Mo.); VG Mass Lab (Danvers, Mass.); and Zymed (Zymed Laboratories, San Francisco, Calif.).

In the examples that follow, the materials used were obtained from the following sources unless otherwise indicated.

DMEM and other media, non-essential amino acids, penicillin G, streptomycin, DL-alpha-tocopherol, and Hanks' BSS were obtained from Gibco BRL. Fetal bovine serum was obtained from Hyclone. Millicell™ CM and PCF culture inserts and the Millicell™ ERS device were obtained from Millipore. Uncoated and commercially coated (unpolymerized collagen type I, 200 $\mu$g/cm$^2$; fibrillar collagen (polymerized type I collagen), 200 $\mu$g/cm$^2$; collagen type IV, 15 $\mu$g/cm$^2$; laminin, 25 $\mu$g/cm$^2$; Matrigel, 2.86 mg/cm$^2$) track etched PET (polyethylene terephthalate) inserts, Matrigel, Growth Factor Reduced Matrigel (used at 2.86 mg/cm$^2$), Dispase, ITS™, and ITS+™ were obtained from Collaborative Biomedical Products. 1$\alpha$,25-dihydroxyvitamin $D_3$, 25-hydroxyvitamin $D_3$, and unhydroxylated vitamin $D_3$ were obtained from Calbiochem. N-methyl-N-(t-butyl-dimethylsilyl)trifluoroacetamide was obtained from Pierce Chemical, while $\beta$-glucuronidase (G-7770) and other chemicals were obtained from Sigma and were of tissue culture or molecular biology grades where appropriate. Midazolam, $^{15}N_3$-midazolam, 4-hydroxymidazolam, 1'-hydroxymidazolam, and 1'-[$^2H_2$], 1'-hydroxymidazolam were received from Roche (Dr. Bruce Mico).

Additional stable isotope-labeled internal standards ($^{15}N_3$-1'-hydroxymidazolam and $^{15}N_3$-4-hydroxymidazolam) were generated from an incubation of $^{15}N_3$-midazolam with human liver microsomes. Briefly, human liver microsomes, containing 6 nmol total cytochrome P450, were incubated with 100 $\mu$g $^5N_3$-midazolam and 12 mg NADPH in 100 mM potassium phosphate buffer, pH 7.4, for 10 min at 37° C. The reaction (8 mL final volume) was stopped by the addition of 8 mL 100 mM Na$_2$CO$_3$, pH 12.5. $^{15}N_3$-labeled hydroxy products were extracted twice with 20 mL ethyl acetate, and the solvent was removed under nitrogen. The remaining solid was redissolved in 20 mL methanol and stored in aliquots at −20° C.

Stock solutions of 1$\alpha$,25-(OH)$_2$-$D_3$, 25-(OH)-$D_3$ and $D_3$ were made in absolute ethanol or dimethyl sulfoxide; test and control cultures contained 0.1–0.2% ethanol or 0.2% dimethyl sulfoxide. The midazolam stock solution was 4 mM in dimethyl sulfoxide.

The following general procedures were used in the examples that follow unless otherwise indicated.

Harvesting for mRNA Analyses and RNA Isolation

The medium was aspirated and the culture inserts were washed three times with Hanks' BSS containing 15 mM HEPES. Chomczynski and Sacchi's denaturing solution was applied to the monolayer (333 $\mu$L/cm$^2$ of insert membrane surface area). The denaturing solution contains 4M guanidinium thiocyanate, 25 mM sodium citrate (pH 7), 0.5% sarcosyl, and 0.1M 2-mercaptoethanol [Chomczynski and N. Sacchi, Anal. Biochem. 162:156–159 (1987)]. After 5 minutes, the cell lysate was transferred to a microcentrifuge tube and kept at −80° C. pending further processing. At a later time, the lysate was thawed quickly at 65° C., and total RNA was isolated according to the protocol of P. Chomczynski and N. Sacchi. Briefly, extraction was performed using the denaturing solution, 2M sodium acetate (pH 4), phenol, and chloroform (1:0.1:1:0.2). Next, precipitation was effected with 2 volumes of ethanol. Resolubilization and reprecipitation was then performed using the denaturing solution and 2 volumes of ethanol. Finally, a 75% ethanol wash was performed, and resolubilization was conducted using DEPC-treated deionized water. The reagent volumes were adjusted proportionately as appropriate for the initial lysate volume.

mRNA Analyses cDNA was prepared from the total RNA using reverse transcriptase from avian myeloblastosis virus (Seikagaku America). Specifically, cDNA was prepared from RNA samples by incubating 1 μg total RNA at 41° C. for one hour with 35 U of reverse transcriptase in a 50 μL reaction mixture containing 50 mM Tris-HCl (pH 8.3), 50 mM potassium chloride, 10 mM dithiothreitol, 13 μM oligo (12–18) dT, and 0.5 mM each dATP, dTTP, dGTP, and dCTP [P. Schmiedlin-Ren et al. Biochem. Pharmacol. 46:905–918 (1993)]. The polymerase chain reaction was performed on 1 μL of a 1:10 dilution in water of a prepared cDNA.

Primer sequences for amplification of CYP3A3, CYP3A4, CYP3A5, and

CYP3A7 (product sizes 619, 382, 350, and 469 bp, respectively) cDNAs are set forth in Table 3.

included in each PCR run and was confirmed to be negative when run on the gel. PCR products were judged to be of the size appropriate for amplification of the specific cDNA by comparison with molecular weight standards included on each gel. The sequence of a PCR product produced from Caco-2 cell cDNA by each primer pair was determined by the Sanger method [F. Sanger et al., Proc. Nat]. Acad. Sci. U.S.A. 74:5463–5467 (1977)] using the plasmid pCR™II (Invitrogen) and was confirmed to be consistent with the published specific cDNA sequence.

The technique of quantitative competitive PCR was used to measure levels of CYP3A4 mRNA [see M. Becker-Andre and K. Hahlbrock, Nucleic Acids Res. 17:9437–9446

TABLE 3

| Gene | Sense Primers | Anti-Sense Primers |
| --- | --- | --- |
| CYP3A3 | 5' GGC TAT CAC AGA TCC TGA CAT GAT CAA ACT 3' (SEQ ID NO:1) | 5' TGT GGG ACT CAG TTF CTT TTG AAT TCT TAT 3' (SEQ ID NO:2) |
|  | 5' TGG ACC CAG AAA CTG CAT TGG CAT GAG GTT 3' (SEQ ID NO:3) | 5' ACT CTA CAC AGA CAA TGA GAG AGC TCC GGA 3' (SEQ ID NO:4) |
|  |  | 5' CAT TGG ATG AAG CCA TCT CAT TTC AGA GTC 3' (SEQ ID NO:5) |
| CYP3A4 | 5' CCT TAC ACA TAC ACA CCC TTT GGA AGT 3' (SEQ ID. NO:6) | 5' AGC TCA ATG CAT GTA CAG AAT CCC CGG TTA 3' (SEQ ID NO:7) |
| CYP3A5 | 5' CCC AGT TGC TAT TAG ACT TGA 3' (SEQ ID NO:8) | 5' TTC TGG TTG AAG AAG TCC TTG CGT GTC 3' (SEQ ID NO:9) |
| CYP3A7 | 5' AGT ATA GAA AAG TCT GGG GTA TTT ATG ACT 3' (SEQ ID NO:10) | 5' TAT TGA GAG AAC GAA TGG ATC TAA TGG 3' (SEQ ID NO:11) |

These are the same primer sequences previously used by J. C. Kolars et al. [Pharmacogenetics 4:247–259 (1994)], except that a different antisense primer (SEQ ID NO:9) was used for CYP3A5, and the first sense primer for CYP3A3 was paired with the second antisense primer used by Kolars et al. (i.e., in the present invention, SEQ ID NO:1 was paired with SEQ ID NO:2).

The primers for mdr-1 cDNA amplification were 5' GTC ATT GTG GAG AAA GGA AAT CAT G 3' (SEQ ID NO:12) and 5' ATT CCA AGG GCT AGA AAC AAT AGT G 3' (SEQ ID NO:13), product size 478 bp [C. Chen et al., J. Biol. Chem. 265:506–514 (1990)]. The primers for IFABP cDNA amplification were 5' AGG AAG CTT GCA GCT CAT GAC AAT TTG AAG 3' (SEQ ID NO:14) and 5' AGT ATT CAG TTC GTT TCC ATT GTC TGT CCG 3' (SEQ ID NO:15), product size 231 bp [D. A. Sweetser et al., J. Biol. Chem. 262:16060–16071 (1987)]. The primers used for villin cDNA amplification were 5' CAG CTA GTG AAC AAG CCT GTA GAG GAG CTC 3' (SEQ ID NO:16) and 5' GCC ACA GAA GTT TGT GCT CAT AGG CAC ATC 3' (SEQ ID NO:17), product size 303 bp [M. Arpin et al., J. Cell Biol. 107:1759–1766 (1988). Of note, if CYP3A5 and CYP3A3 are organized in the same fashion as CYP3A4 [H. Hashimoto et al., Eur. J. Biochem. 218:585–595 (1993)] and CYP3A 7 [S. Itoh et al., Biochim. Biophys. Acta 1130:133–138 (1992)], then all synthetic oligonucleotide primer pairs that were used spanned at least one intron.

The 25 μL PCR reaction mixture contained 10 mM Tris-HCl (pH 8.3), 50 mM potassium chloride, 1.6 mM magnesium chloride, 2 mM dithiothreitol, 12.5 pmol each oligonucleotide primer, 1.7 units of Thermus aquaticus (Taq) DNA polymerase (Amplitaq™, Applied Biosystems), and 0.1 mM each dATP, dTTP, dGTP, and dCTP. Each thermal cycle consisted of 95° C. for 1 min, then 65° C. for 1 min 15 sec; after completing all cycles, a 10 min extension step at 65° C. was performed. The number of cycles performed in each PCR reaction is set forth below in the Examples.

PCR products were electrophoresed on agarose gels and stained with ethidium bromide. A reagent control was (1989); G. Gilliland et al., Proc. Natl. Acad. Sci. U.S.A. 87:2725–2729 (1990)]. An internal standard for quantitative competitive PCR of CYP3A4 cDNA was prepared by inserting a 30 base pair segment into the cDNA sequence to be amplified. PCR reaction mixtures were prepared by combining serial dilutions of a known amount of the standard cDNA and constant amounts of the unknown cDNA. The two cDNAs were amplified together and the products were separated on agarose gels. After staining with ethidium bromide, the two bands were quantitated densitometrically. An equivalence point (at which the densities of the standard and unknown bands are of equal optical density) was determined; the concentration of the unknown is equal to that of the standard at the point of equivalence. Neither the identity of the specific sequence inserted nor its insertion site is important provided that the competitive template and the CYP3A4 cDNA are amplified with equal efficiency; in the present situation, it is believed that the insertion of the 30 base pair segment into the standard does not significantly alter amplification efficiency.

Harvesting for Immunoblots

The medium was aspirated and the inserts were washed three times with Hanks' BSS containing 15 mM HEPES. Cells grown on Matrigel- (or Growth Factor Reduced Matrigel-) coated inserts were removed from the membranes using Dispase according to the manufacturer's protocol. Thereafter, 5 mM EDTA in normal saline containing 1 mM PMSF and 1 mM benzamidine was added to inhibit further digestion. The cell suspension was transferred to a microcentrifuge tube and pelleted by centrifugation at 325 g. The pellets were washed three times with Hanks' BSS containing 15 mM HEPES, 1 mM PMSF, and 1 mM benzamidine. The final pellet was resuspended in a solution of 20% v/v glycerol, 100 mM Tris HCl (pH 7.4), 10 mM EDTA, 1 mM dithiothreitol, I mM PMSF, 1 mM benzamidine, and 100 μg/mL aprotinin and homogenized in a conical ground glass tissue grinder with 20 passes of a ground glass pestle. The homogenate was subjected to 10 seconds of sonication and was then kept at −80° C. until analysis.

Cells grown on uncoated inserts or inserts coated with non-Matrigel matrices were harvested by scraping into Hanks' BSS containing HEPES and protease inhibitors, washed three times, and then homogenized, sonicated, and frozen as described above.

Immunoblots

The protein concentrations of the cell homogenates were measured by the standard protein-dye binding method using BSA standards [M. M. Bradford, Anal. Biochem 72:248–254 (1976)]. The homogenates were electrophoresed in polyacrylamide gels containing 0.1% SDS, and the separated proteins were electrophoretically transferred to nitrocellulose. Nonspecific binding sites were blocked using 0.3% Tween 20 and 5% nonfat dry milk (Carnation) in Tris buffered saline. 0.3% Tween 20 was present during primary and secondary antibody incubations and the intervening Tris buffered saline washes, while 0.25% nonfat dry milk was also present during the secondary antibody incubation and all washes until just prior to the application of detection reagents.

CYP1A1 was detected using a polyclonal goat antibody (Gentest) developed against rat CYP1A1 and CYP1A2. This antibody has also been shown to detect the human forms of these proteins. CYP3A proteins were detected using a mouse monoclonal antibody ("13-7-10") obtained from Dr. Pierre Kremers (Universite de Liege, Liege, Belgium). This monoclonal antibody may be produced by immunizing Balb/c mice by intraperitoneal injection with 50 $\mu$g of cytochrome P-450III A diluted in 200 $\mu$L isotonic sodium chloride and mixed with 200 $\mu$L of complete Freund adjuvant. The mice are boosted with 10 $\mu$g P-450III A three weeks thereafter and three days before fusion. Next, spleen cells are fused with myeloma cells and the hybrids are cultured. Positive cultures can be cloned by diluting to single cell density, and production clones are then grown in flasks before being implanted intraperitoneally in the mice. About two weeks thereafter, ascitic fluid is collected, centrifuged, and the immunoglobulins are purified (e.g., by DEAE-affigel blue chromatography) [P. Beaune et al, Biochem. Pharmacol. 34:3547–3552 (1985)]. This antibody detects all known forms of human CYP3A.

CYP3A5 was detected using an immunoadsorbed polyclonal rabbit antibody obtained from Dr. Steven A. Wrighton (Eli Lilly). The antibody may be generated by injecting rabbits subcutaneously with 100 $\mu$g of P450IIIA5 in 0.75 mL of phosphate-buffered saline in an emulsion made with 1.25 mL of Freund's complete adjuvant. Four weeks later, 50 $\mu$g of P450IIIA5 (in the same preparation) is injected. Finally, eight weeks from the initial injection, 50 $\mu$g of P450IIIA3 in 300 $\mu$L of phosphate-buffered saline is injected intravenously into the rabbits' ear vein. Serum was obtained 10 weeks following the initial immunization and weekly thereafter. The IgG fraction was then isolated and antibodies specific to CYP3A5 were isolated by adsorption of contaminating antibodies to sepharose-bound CYP3A4 [S. A. Wrighton et al., Mol. Pharmacol. 38:207–213 (1990).

CYP2D6 was detected using a polyclonal rabbit antibody developed against unique antigenic peptides and was obtained from Dr. Alastair Cribb (Merck Research Laboratories, West Point, Pa.). This antibody can be produced according to the following procedure [A. Cribb et al., Drug Metab. Dispos. 23:671–675 (1995)]. Briefly, two peptide sequences that correspond to sequences within the major thirty-three amino acid sequence of CYP2D6 are injected into rabbits (peptide 1: DPAQPPRDLTEAFLA; peptide 2: LLTEHRMTWDPAQPPRDLTE conjugated to keyhole limpet hemocyanin). The immunization schedule is as follows: 500 $\mu$g immunogen in Freund's complete adjuvant on day 0, 250 $\mu$g in Freund's incomplete adjuvant on days 22 and 43, 100 $\mu$g in Freund's incomplete adjuvant on days 64, 85, and 106, then approximately every 28 days. Sera is collected following three immunizations.

NADPH cytochrome P450 reductase and cytochrome $b_5$ were detected using polyclonal rabbit antibodies developed against the specific rat proteins, but which were found to also recognize the human forms of these proteins. NADPH cytochrome P450 reductase was purified from phenobarbital-induced adult rat liver microsomes [C. A. Lee et al., Drug Metab. Dispos. 19:348–353 (1991)].

Rat cytochrome $b_5$ was purified from adult rat liver following a method identical to that previously described for the purification of rabbit cytochrome $b_5$ [K. E. Thummel et al., Biochem. Pharmacol. 45:1563–1569 (1993)]. Briefly, rat liver microsomal protein was isolated by differential centrifugation from the livers of phenobarbital-induced rats. About 1000 mg of total microsomal protein was solubilized in phosphate buffer containing 0.2% Emulgen 911. The late-eluting protein fraction from lauryl-Sepharose chromatography containing cytochrome $b_5$ was dialyzed against 5 mM potassium phosphate buffer, pH 7.5, containing 25% glycerol, 0.5% Emulgen 911, 0.1 mM DTT and 0.1 mM EDTA (subsequent elution buffers contained the same components). Thereafter, the dialyzed cytochrome $b_5$ fraction was subjected to DEAF-Sepharose chromatography, washing with 400 mL of 50 mM potassium phosphate buffer. The cytochrome $b_5$ eluted from the column approximately midway through a linear 50 to 500 mM potassium phosphate gradient (1000 mL total volume). Thereafter, the elution fractions containing $b_5$ were pooled and dialyzed against 20 mM Tris-acetate buffer, pH 7.5, with 20% glycerol. Next, the cytochrome $b_5$ was loaded onto an anion exchange HPLC column, the column washed with equilibration buffer, and the protein eluted from the column about midway through a linear 0 to 500 mM sodium acetate gradient in Tris-acetate equilibration buffer (500 mL total volume). Finally, the purer fractions (as indicated by sodium dodecyl sulfate-polyacrylamide gel electrophoresis) were pooled, subjected to cholate-Emulgen 911 exchange on a hydroxyapatite column, and dialyzed against 20 mM potassium phosphate, pH 7.4, 25% glycerol.

Rabbit polyclonal antibody was produced against each antigen in female New Zealand white rabbits. Animals received an initial subcutaneous injection (250 $\mu$g NADPH cytochrome P450 reductase or 200 $\mu$g cytochrome $b_5$) in Freund's complete adjuvant followed three weeks later by an identical booster dose in Freund's incomplete adjuvant. Peripheral blood was collected over the next 20 weeks, and serum IgG was isolated [E. D. Kharasch and K. E. Thummel, Anesth. Analg. 76:1033–1039 (1993)].

P-glycoprotein was detected using a polyclonal rabbit antibody (Oncogene Science), and villin was detected using a mouse monoclonal antibody (Chemicon International). Intestinal fatty acid binding protein (IFABP) and liver fatty acid binding protein (LFABP) were detected using polyclonal rabbit antibodies developed against rat proteins but which have been shown to detect the human forms of these proteins. These antibodies, obtained from Dr. Jeffrey Gordon (Washington University School of Medicine, St. Louis, Mo.) are raised against IFABP or LFABP expressed in *E. coli* [S. L. Carroll et al., Gastroenterology 99:1727–1735 (1990); J. B. Lowe et al., J. Biol. Chem. 262:5931–5937 (1987)].

Secondary antibodies of appropriate specificities conjugated with horseradish peroxidase were obtained commercially (rabbit anti-mouse IgG and goat anti-rabbit IgG/A/M from Zymed and mouse anti-goat IgG/A/M from Pierce). Binding of secondary antibodies was detected using the enhanced chemiluminescence (ECL™) reagents and film from Amersham.

In some cases, immunoblot protein concentrations were determined by computer-aided densitometry. When this procedure was conducted, optical densities were performed on a Macintosh (Apple) computer using the publicly available NIH Image program (developed at the U.S. National Institutes of Health and available on the Internet at http://rsb.info.nih.gov/nih-image/). Individual exposures were scanned into binary images with a ScanJetIIc color scanner (Hewlett-Packard). An optical density-concentration standard curve was prepared using the bands from second loaded serial dilutions of purified CYP3A4 protein, and the optical densities of unknowns were converted to quantitative numbers by comparison to this curve. This allowed for correction of the nonlinearity of ECL light output and ECL Hyperfilm.

Midazolam, 1'-Hydroxymidazolam, and 4-Hydroxymidazolam Assays

As set forth in detail in the examples that follow, the principal means to assess CYP3A catalytic activity in Caco-2 cell cultures was measurement of the rate and extent of midazolam 1'-hydroxylation; midazolam (MDZ) serves as a substrate for CYP3A [T. D. Kronbach et al., Mol. Pharmacol. 36:89–96 (1989)]. All culture samples were analyzed in duplicate and the mean of the two measurements is reported. For each of the midazolam metabolism studies, the medium was aspirated and the culture inserts were washed three times with Hanks' BSS. Next, 1.5 mL of fresh complete differentiation medium was placed on each side of the insert, with 4 $\mu$M midazolam present in the medium placed on only one side of the monolayer (usually the apical medium). The incubation media did not contain vitamin D (except that contributed by the 5% FBS). After variable times (described in the examples that follow), the amount of 1'-OH-MDZ was measured in the apical, in the basolateral, or in the combined apical plus basolateral medium from each culture and the rate of formation calculated. The type of measurement depended, in part, on whether only the rate of metabolite formation was being determined or if the distribution across the monolayer was also being determined.

For quantitation of 1'-hydroxymidazolam (1'-OH-MDZ), 0.2–1.0 mL of medium removed from the apical or basolateral compartment of a Caco-2 cellculture was diluted with water to a volume of 1 mL. To this was added 1 mL of 50 mM $Na_2CO_3$, pH 12.5, and 20 ng of 1'-[$^2H_2$],1'-hydroxymidazolam internal standard. For the analysis of midazolam (MDZ), 0.02 mL of culture medium was diluted to a volume of 1 mL. To this was added 1 mL of 50 mM $Na_2CO_3$, pH 12.5, and 40 ng of $^{15}N_3$-midazolam internal standard. Standards were also prepared in duplicate. Known amounts of MDZ and 1'-OH-MDZ (1–50 ng) were combined with 100 mM potassium phosphate buffer, pH 7.4. To this was added 1 mL of 50 mM $Na_2CO_3$, pH 12.5, and the appropriate amount of stable isotope-labeled internal standard.

Unknowns and standards were extracted with 5 mL ethyl acetate and the upper organic layer transferred to clean tubes. The solvent was evaporated to dryness under a stream of nitrogen. The remaining solvent was reconstituted in 100 $\mu$L derivatizing reagent (10% N-methyl-N-(t-butyldimethylsilyl)trifluoroacetamide in acetonitrile). Samples were transferred to glass autoinjector vials, sealed, and heated at 80° C. for two hours before analysis by gas chromatography/selective ion mass spectrometry (VG Mass Lab Trio 1000 interfaced to a Hewlett-Packard 5890 Series II gas chromatograph) [M. Paine et al., Clin. Pharmacol. Ther. 60:14–24 (1996)].

EXAMPLE 1

Selection Of Caco-2 Cells

This example describes the selection of Caco-2 cell clones with high CYP3A4 expression and favorable growth characteristics. Cells from the specific clone selected based on the experiments from this example were further characterized in the experiments reported in the subsequent examples.

Preparation Of Clones

Caco-2 cells (ATCC; ATCC Assession No. HTB37) were obtained at passage 19 and grown in plastic tissue culture dishes in a medium consisting of DMEM containing 25 mM glucose and 2 mM L-glutamine, and supplemented with 0.1 mM non-essential amino acids, 45 nM DL-alpha-tocopherol, 100 U/mL sodium penicillin G, and 100 $\mu$g/mL streptomycin. Complete growth medium was then prepared by adding 20% heat-inactivated FBS. When the cells reached 80% confluence, they were removed using 0.1% trypsin/0.537 mM EDTA, diluted 1:3, and re-seeded onto fresh tissue culture dishes. All cultures were maintained in a humidified 37° C. incubator with a 5% carbon dioxide in air atmosphere. Media were changed every two to three days.

To obtain genetic homogeneity among the cells, five clones were prepared from the parent Caco-2 cell line at passage 27 by limiting dilution. Briefly, a dilute suspension of passage 27 Caco-2 cells was prepared and distributed into the wells of microtiter plates such that each well was expected to receive 0.5–1 cell; these wells were observed microscopically and the cells from wells which appeared to contain only a single colony were propagated further in culture. For the experiments set forth hereafter the clones were used at passages 9 to 16, whereas the parent cell line was used at passage 24 or 27.

The cells were seeded at $6 \times 10^5$ cells/cm² onto the membranes of culture inserts using complete growth medium. Millicel™ CM (teflon membrane; 0.4 $\mu$m pore size; Millipore) culture inserts were primarily used; as described further below, other inserts were also used (e.g., PET [0.1 $\mu$m pore size] inserts). The following day the membranes were washed three times and fresh medium was added. Subsequent medium changes were at two-to-three day intervals. After reaching confluence, the cells were cultured an additional two weeks in complete differentiation medium.

Because the Millicell™ CM inserts require an extracellular matrix coating for cell adherence, the inserts were coated according to the manufacturer's instructions with a dried film of Matrigel. Briefly, the Matrigel was thawed on ice, diluted with ice-cold sterile water to 1.35 mg/mL, and dispensed (225 $\mu$g/cm²) into pre-cooled inserts using pre-cooled pipet tips. The inserts were then allowed to dry overnight in a laminar flow hood.

RNA Preparation and Amplification of CYP3A4 cDNA

In this example and in the examples set forth below, protein analysis and metabolic activity assays were performed from a single 30 mm insert per time point or per culture condition variation, and RNA analysis was performed from a separate 12 mm or 10 mm insert.

RNA was prepared from cells of the five clones produced by limiting dilution by the procedure described above for RNA isolation. Thereafter, RT-PCR was performed (by the method described above) using a pair of synthetic oligonucleotide primers designed to specifically amplify CYP3A4 cDNA (see Table 3; SEQ ID NO:6 (sense) and SEQ ID NO:7 (antisense). The relative band intensities of the RT-PCR products (not shown) on ethidium stained agarose gels indicated that all five of the clones appeared to express greater levels of CYP3A4 mRNA than did the parent cell line. The clone (clone #5) which appeared to have the highest level of expression of CYP3A4 mRNA was found to have poor growth characteristics. Therefore, a clone (clone #7) with an intermediate level of CYP3A4 mRNA expression was selected and used for each of the experiments described below unless otherwise indicated.

EXAMPLE 2

Defining Favorable Culture Conditions

This example is directed at the identification of culture conditions which favored expression of CYP3A4 by Caco-2 cells. The experiments of this example utilized RT-PCR to assess relative levels of CYP3A4 mRNA, immunoblotting to assess relative levels of CYP3A protein, or midazolam 1'-hydroxylation to assess CYP3A catalytic activity, in two week post-confluent cells. The cells had been grown with or without Matrigel or other extracellular matrices, or had been exposed to test compounds (described below) added to the differentiation medium beginning at the time of confluence.

The Effect of the Presence or Absence of Extracellular Matrix Coatings

A separate experiment was performed in order to compare the effect of the presence or absence of extracellular matrix. For this experiment, Millicell™ PCF inserts (polycarbonate membrane; 3.0 µm pore size), which do not require a matrix coating for cell adherence, were used with and without a Matrigel coating.

Upon achieving confluence (transepithelial resistance of $\geq 250$ Ohm○cm$^2$ [see M. G. Traber et al., J. Lipid Res. 28:1350–1363 (1987)] as measured using a Millicell™ ERS device), the basic medium was additionally supplemented (to the indicated final concentrations) with sodium selenite (0.1 µM), zinc sulfate (3 µM), and ferrous sulfate (5 µM). Complete differentiation medium was then prepared by adding 5% heat-inactivated FBS.

The achievement of confluence was delayed on the Matrigel-coated inserts (average ~12–25 days) as compared to uncoated polycarbonate inserts (~7 days). However, the levels of CYP3A4 mRNA (as well as villin and IFABP mRNAs) two weeks post-confluence generally appeared to be higher when using Matrigel coated inserts (data not shown). For this reason, Matrigel was used in subsequent cultures.

The Effect of Various Extracellular Matrix Coatings on Inserts

As indicated above, the Millicell™ CM (Millipore) inserts were coated with a dried film of Matrigel. The amount and nature of the Matrigel coating influenced whether a confluent monolayer was produced. For example, in initial studies, Caco-2 cells demonstrated a marked tendency to pull away from the perimeter of the Matrigel-coated inserts; the cells formed complex structures rather than maintaining a confluent monolayer pattern of growth, and thus these cultures were unusable. When the amount of Matrigel/cm$^2$ of surface area of the inserts was increased or when the Matrigel was used as a gel instead of a dried film, the pulling away worsened.

The effect of various other extracellular matrices on cell growth was also determined. For these experiments, Caco-2 cells were grown on PET inserts (1 µm pore size) commercially coated (Collaborative Biomedical Products) with Growth Factor Reduced Matrigel, laminin, collagen type IV, collagen type I, and polymerized collagen type I (fibrillar collagen). The results (not shown) demonstrated a monolayer pattern of growth and a more rapid achievement of confluence than cells grown on Matrigel. On the inserts commercially coated with unpolymerized collagen type I and, to a lesser degree, on the inserts coated with collagen type IV, the Caco-2 cells demonstrated dome formation (results not shown). The dome formation indicates that there was impairment of water and electrolyte movement across the membrane. Therefore, the inserts commercially coated with unpolymerized collagen type I and collagen type IV are not preferred for use in conjunction with the present invention because the results obtained would not be predictive of drug absorption in humans.

The Effect of Various Additives to Complete Differentiation Medium

For this experiment, the cells were grown on Millicell™ CM inserts which had been coated with a dried film of Matrigel. The cells were grown to confluence in complete growth medium, and then for an additional two weeks in complete differentiation media.

The differentiation medium of some cultures was supplemented with retinol acetate (vitamin A, 0.3 µM), menadione sodium bisulfite (vitamin K, 145 nM), delta-aminolevulinic acid (50–100 µM), sodium pyruvate (1 mM), sodium butyrate (2 mM, in the presence or absence of vitamin $D_2$), vitamin $D_2$ (ergocalciferol, 0.63 µM), 1α,25-(OH)2-$D_3$(1α, 25-dihydroxycholecalciferol, 0.63 µM),25-(OH)-$D_3$, or $D_3$. The cells from all experiments were maintained in their respective differentiation media for two weeks post-confluence. Thereafter, the cells were used for midazolam metabolism studies and/or harvested for analysis of protein or mRNA (described below).

Vitamin A, vitamin K, vitamin $D_2$, delta-aminolevulinic acid, sodium butyrate, or sodium pyruvate did not appear to enhance CYP3A4 mRNA expression (data not shown). However, addition of 1α,25-(OH)2-$D_3$ to the medium was found to result in a dramatic increase in the expression of CYP3A4 mRNA.

Comparison of Complete Differentiation Media

A comparison was made using several different cell culture media as the basic component of the 5% FBS-containing differentiation medium used during the two weeks post-confluence. All of the complete differentiation media were formulated to contain equal amounts of glucose, L-glutamine, selenium, zinc, and vitamin E; all of the media were also supplemented with 0.25 µM 1α,25-(OH)$_2$-$D_3$. The results showed that CYP3A catalytic activity was greater in cultures grown in DMEM, DMEM/F12 (1:1), or Williams' E based medium than in cultures grown in Iscove's, Iscove's/F12/NCTC135 (5:5:1), RPMI 1640, McCoy's 5A, Waymouth 752/1, Waymouth with 0.1 mM non-essential amino acids, Medium 199, CMRL 1066, or CMRL/F12 (4:1) based medium (results not shown). However, the differences in catalytic activity among cells grown in the various media were less than 4-fold. Review of the media components did not reveal any single factor shared by DMEM and Williams' E media which is not also present in one or more of the other media which did not perform as well.

The most striking result from the experiments described above was the finding that addition of $1\alpha,25\text{-(OH)}2\text{-D}_3$ to the medium resulted in a dramatic increase in the expression of CYP3A4 mRNA. This effect was further evaluated in the examples described below.

EXAMPLE 3

The Dose-Response Effect Of Various $1\alpha,25\text{-(OH)}_2\text{-D}_3$ Treatment Regimens As indicated in the preceding example, the addition of $1\alpha,25\text{-(OH)}_2\text{-D}_3$ to the culture inserts profoundly increased the expression of CYP3A4 mRNA. The experiments of this example further delineate that result by examining the effect of various $1\alpha,25\text{-(OH)}_2\text{-D}_3$ treatment regimens on CYP3A4 mRNA expression.

A dose-response experiment was performed by administering concentrations of $1\alpha,25\text{-(OH)}_2\text{-D}_3$ spanning the originally tested 0.63 $\mu$M concentration (see Example 2). Treatment of Caco-2 cells grown on Matrigel-coated teflon culture inserts was initiated at the time of confluence and continued for two weeks. Total RNA was then prepared as described above and subjected to RT-PCR using synthetic oligonucleotide primer pairs designed to selectively amplify fragments of the indicated cDNAs (see Table 3). The numbers of PCR cycles were as follows: CYP3A4, 36; CYP3A5, 33; CYP3A7, 39; mdr-1, 34; IFABP, 32; and villin, 27. One culture was used for each of the following concentrations of $1\alpha,25\text{-(OH)}_2\text{-D}_3$: 0.05, 0.1, 0.25, 0.5, 0.75, and 1.0 ($\mu$M).

FIG. 1 is an ethidium bromide stained agarose gel indicating the changes in Caco-2 cell levels of specific mRNAs in response to treatment with varying doses of $1\alpha,25\text{-(OH)}_2\text{-D}_3$. PCR was performed twice with each pair of primers and the results shown are representative. As indicated by FIG. 1, $1\alpha,25\text{-(OH)}_2\text{-D}_3$ resulted in increased CYP3A4 mRNA expression at all concentrations used (0.05–1.00 $\mu$M). An attempt was made to quantitate the fold increase in CYP3A4 mRNA using serial dilutions of an internal standard for competitive amplification and titration (using the methods described above). Though precise quantitation of the fold induction was difficult due to the very low levels of CYP3A4 mRNA present in untreated cells, it appeared that a 40-to-80 fold increase had occurred.

FIG. 1 also indicates that expression of the closely related CYP3A5 and CYP3A7 mRNAs [see D. R. Nelson et al., Pharmacogenetics 6:1–42 (1996)] also appeared to increase in response to $1\alpha,25\text{-(OH)}_2\text{-D}_3$, but to a much lesser degree. CYP3A5 is the major CYP3A enzyme present in normal colon epithelial cells and hence its expression in Caco-2 cells was an expected finding; however, since CYP3A4 is the major CYP3A enzyme present in small bowel enterocytes, the predominance of CYP3A4 in $1\alpha,25\text{-(OH)}_2\text{-D}_3$-treated Caco-2 cells is consistent with an improvement in their characteristic post-confluence differentiation toward a small bowel enterocyte phenotype. Notably, the effect of $1\alpha,\approx\text{-(OH)}_2\text{-D}_3$ was not universal on all mRNAs, as the levels of mdr-1, IFABP, and villin mRNAs did not appear to increase (see FIG. 1). Finally, CYP3A3 mRNA was not detected in treated or untreated Caco-2 cells by RT-PCR.

EXAMPLE 4

The Effect Of Various Vitamin D Analogs

Previous examples determined that the addition of $1\alpha,25\text{-(OH)}_2\text{-D}_3$ dramatically increased the expression of CYP3A4 mRNA. This example addresses whether analogs of that compound ($25\text{-(OH)-D}_3$ and $D_3$) exhibit a similarly favorable effect on expression of CYP3A4 by Caco-2 cells.

Catalytic Activity

For this example, changes in Caco-2 cell levels of expression of CYP3A catalytic activity and immunoreactive protein were determined in response to treatment with varying doses of $1\alpha,25\text{-(OH)}_2\text{-D}_3, 25\text{-(OH)-D}_3$, and $D_3$ (0.0, 0.05, 0.1, 0.25, 0.5, 0.75, and 1.0 $\mu$M concentrations of each). The Caco-2 cells were grown on Matrigel-coated teflon culture inserts and were treated with varying concentrations of the vitamin $D_3$ analogs for two weeks beginning at the time of confluence. At the end of that period, the medium was replaced with medium not containing vitamin D (except that contributed by the 5% FBS). The CYP3A substrate, midazolam (MDZ; 4 EM), was administered to the apical medium. As previously indicated, midazolam was chosen as the probe drug since it is a well-characterized CYP3A4 substrate and because it has been shown to undergo extensive first-pass metabolism in the intestine following oral administration. After 6 hours, the apical and basolateral media were removed separately and analyzed for 1'-OH-MDZ concentration. The cells were then harvested and the homogenates were used for immunoblots.

Figure 2A:
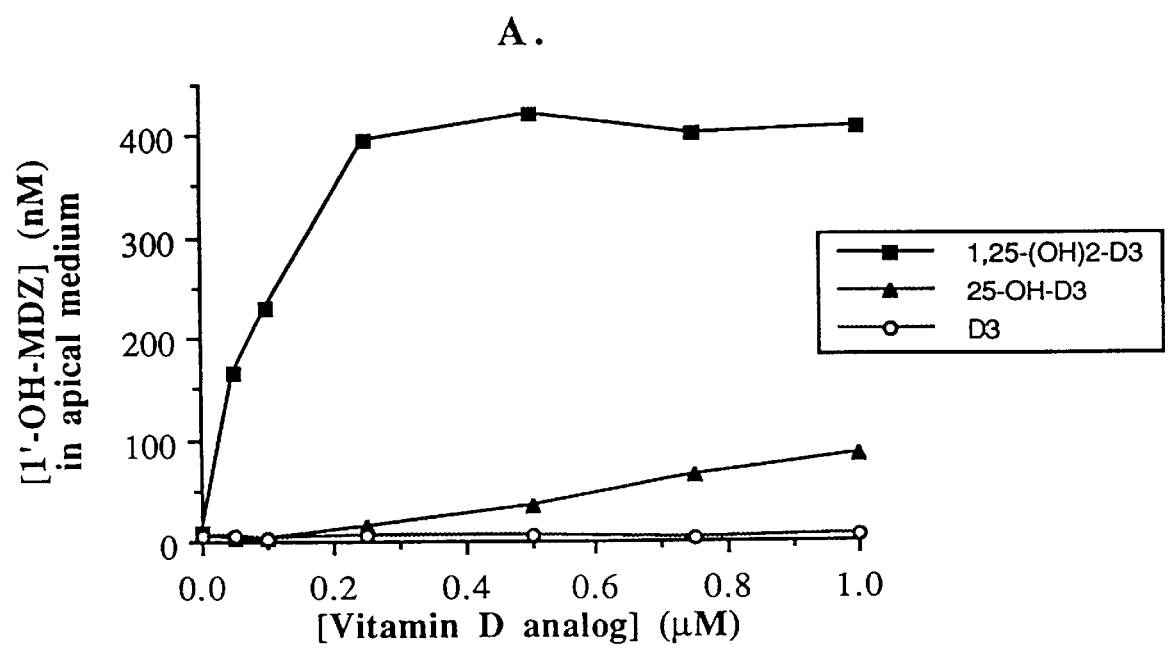
FIG. 2A graphically illustrates the changes in Caco-2 cell levels of expression of CYP3A catalytic activity, as determined by 1'-OH-MDZ formation, in apical media in response to treatment with varying doses of $1\alpha,25\text{-}(OH)_2\text{-}D_3$, 25-(OH)-$D_3$, and $D_3$.
Figure 2B:
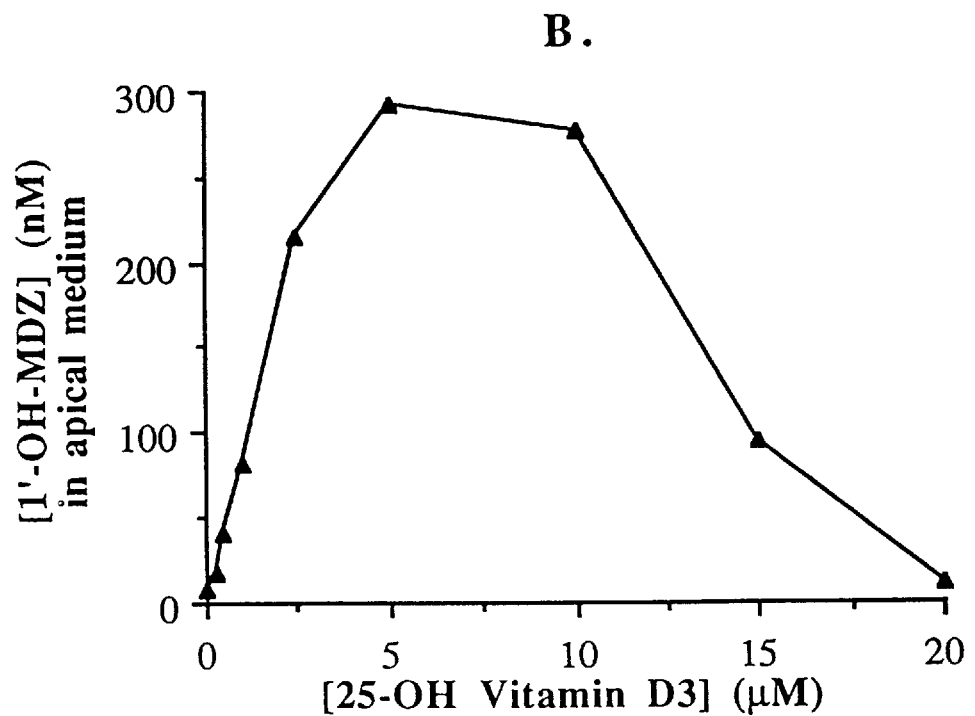
FIG. 2B graphically illustrates the changes in Caco-2 cell levels of expression of CYP3A catalytic activity, as determined by 1'-OH-MDZ formation, in apical media in response to treatment with varying doses of 25-(OH)-$D_3$.

FIG. 2A graphically illustrates the changes in Caco-2 cell levels of expression of CYP3A catalytic activity, as determined by 1'-OH-MDZ formation, in apical media in response to treatment with varying doses of $1\alpha,25\text{-(OH)}_2\text{-D}_3, 25\text{-(OH)-D}_3$, and $D_3$. Referring to FIG. 2A, the solid squares represent the effect of $1\alpha,25\text{-(OH)}_2\text{-D}_3$, the solid triangles represent the effect of $25\text{-(OH)-D}_3$, and the open circles represent the effect of $D_3$. FIG. 2B graphically illustrates the changes in Caco-2 cell levels of expression of CYP3A catalytic activity, as determined by 1'-OH-MDZ formation, in apical media in response to treatment with varying doses of $25\text{-(OH)-D}_3$; the data in FIG. 2B involve higher $25\text{-(OH)-D}_3$ concentrations than those set forth in FIG. 2A.

As set forth in FIG. 2A, the addition of $1\alpha,25\text{-(OH)}_2\text{-D}_3$ resulted in a dramatic increase in the extent of midazolam metabolism (apical concentrations shown). Increases in CYP3A catalytic activity was evident at 0.05 $\mu$M $1\alpha,25\text{-(OH)}_2\text{-D}_3$ and plateaued between 0.25 and 0.5 $\mu$M $1\alpha,25\text{-(OH)}_2\text{-D}_3$. In the initial dose-response experiment using $25\text{-(OH)-D}_3$, CYP3A catalytic activity (and immunoreactive protein, described further below) began to increase at 0.25 $\mu$M $25\text{-(OH)-D}_3$ but the effect had not yet plateaued by 1.0 $\mu$M $25\text{-(OH)-D}_3$. Thus, a dose-response experiment was performed extending to higher concentrations of this agent; the results, set forth in FIG. 2B, indicated that CYP3A catalytic activity was maximal at 5 $\mu$M $25\text{-(OH)-D}_3$ and had substantially declined by 15 $\mu$M, declining still further at 20 $\mu$M $25\text{-(OH)-D}_3$.

Detection of Protein Expression

Figure 2C:
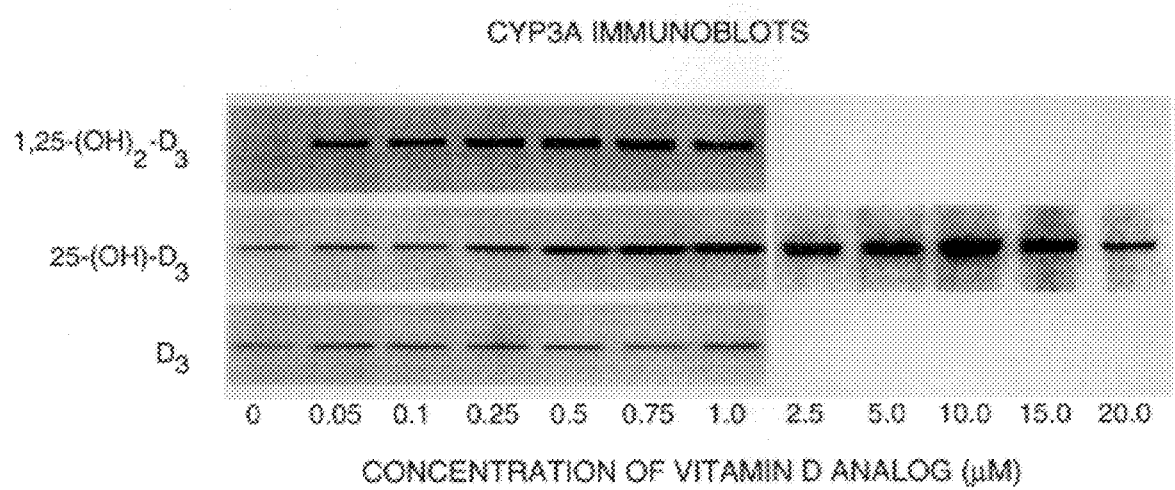
FIG. 2C depicts immunoblots indicating the changes in Caco-2 cell levels of expression of immunoreactive protein in apical media in response to treatment with varying doses of $1\alpha,25\text{-}(OH)_2\text{-}D_3$, 25-(OH)-$D_3$, and $D_3$.

FIG. 2C depicts immunoblots indicating the changes in Caco-2 cell levels of expression of immunoreactive protein in apical media in response to treatment with varying doses of $1\alpha,25\text{-(OH)}_2\text{-D}_3, 25\text{-(OH)-D}_3$, and $D_3$. The immunoblots, generated as previously described, involved cell homogenates (10 $\mu$g protein/lane) developed with a monoclonal antibody which recognizes all known human forms of CYP3A (i.e., the "13-7-10" mouse monoclonal antibody described above). Each point on the graphs in FIGS. 2A and 2B represents one culture and corresponds to one lane on the immunoblots in FIG. 2C. A composite blot from two sets of cultures is shown for 25-(OH)-$D_3$, which required higher doses than $1\alpha,25$-$(OH)_2$-$D_3$ to achieve a maximal response. Analogous to the increases in CYP3A catalytic activity depicted in FIG. 2A, FIG. 2C indicates that immunoreactive protein was evident at 0.05 $\mu$M $1\alpha,25$-$(OH)2$-$D_3$ and plateaued between 0.25 and 0.5 $\mu$M $1\alpha,25$-$(OH)_2$-$D_3$. The maximal CYP3A catalytic activity achieved with 25-(OH)-$D_3$ was not as great as that achieved with $1\alpha,25$-$(OH)_2$-$D_3$. Unhydroxylated $D_3$ had no effect on immunoreactive CYP3A protein or midazolam metabolism (concentrations greater than 1.0 $\mu$M were not examined).

EXAMPLE 5

Expression Of Various Proteins In Response To $1\alpha$, 25-$(OH)_2$-$D_3$ And To 25-$(OH)_2$-$D_3$ This example addresses levels of expression of a variety of proteins by Caco-2 cells in response to varying doses of $1\alpha,25$-$(OH)_2$-$D_3$ and 25-$(OH)_2$-$D_3$. More specifically, levels of expression of CYP3A, CYP3A5, CYP1A1, CYP2D6, cytochrome P450 reductase, cytochrome $b_5$, P-glycoprotein, IFABP, LFABP, and villin were assessed.

Caco-2 cells grown on Matrigel-coated teflon culture inserts were treated with varying concentrations of either $1\alpha,25$-$(OH)_2$-$D_3$ or 25-$(OH)_2$-$D_3$ for two weeks beginning at the time of confluence. Cell homogenates were then prepared as described above and immunoblots were performed; the Caco-2 protein loads were as follows: 10 $\mu$g for CYP3A, CYP3A5, P-glycoprotein, villin; 25 pg for CYP1A1, CYP2D6; 40 $\mu$g for IFABP, LFABP; 80 $\mu$g for NADPH cytochrome P450 reductase, cytochrome $b_5$ (the villin, IFABP, and LFABP served as control proteins).

For comparison, mucosal scrapings from paired human duodenum and jejunum were used to prepare total homogenate and microsomes, as described above. Human duodenal biopsy homogenate protein loads were as follows: 25 $\mu$g for CYP3A, P-glycoprotein, villin; 40 $\mu$g for CYP1A1; 50 $\mu$g for CYP2D6; 60 $\mu$g for IFABP, LFABP; 80 $\mu$g for cytochrome $b_5$. Human liver protein loads were as follows: 3 $\mu$g for CYP1A2, CYP2D6; 10 $\mu$g for cytochrome $b_5$; 12 $\mu$g for CYP3A5; 25 $\mu$g for NADPH cytochrome P450 reductase; 40 $\mu$g for LFABP. Liver microsomes were used except for LFABP for which liver homogenate was used. The appropriate antibodies (i.e., those specific for a particular protein, as described above) were used to develop the immunoblots.

Figure 3:
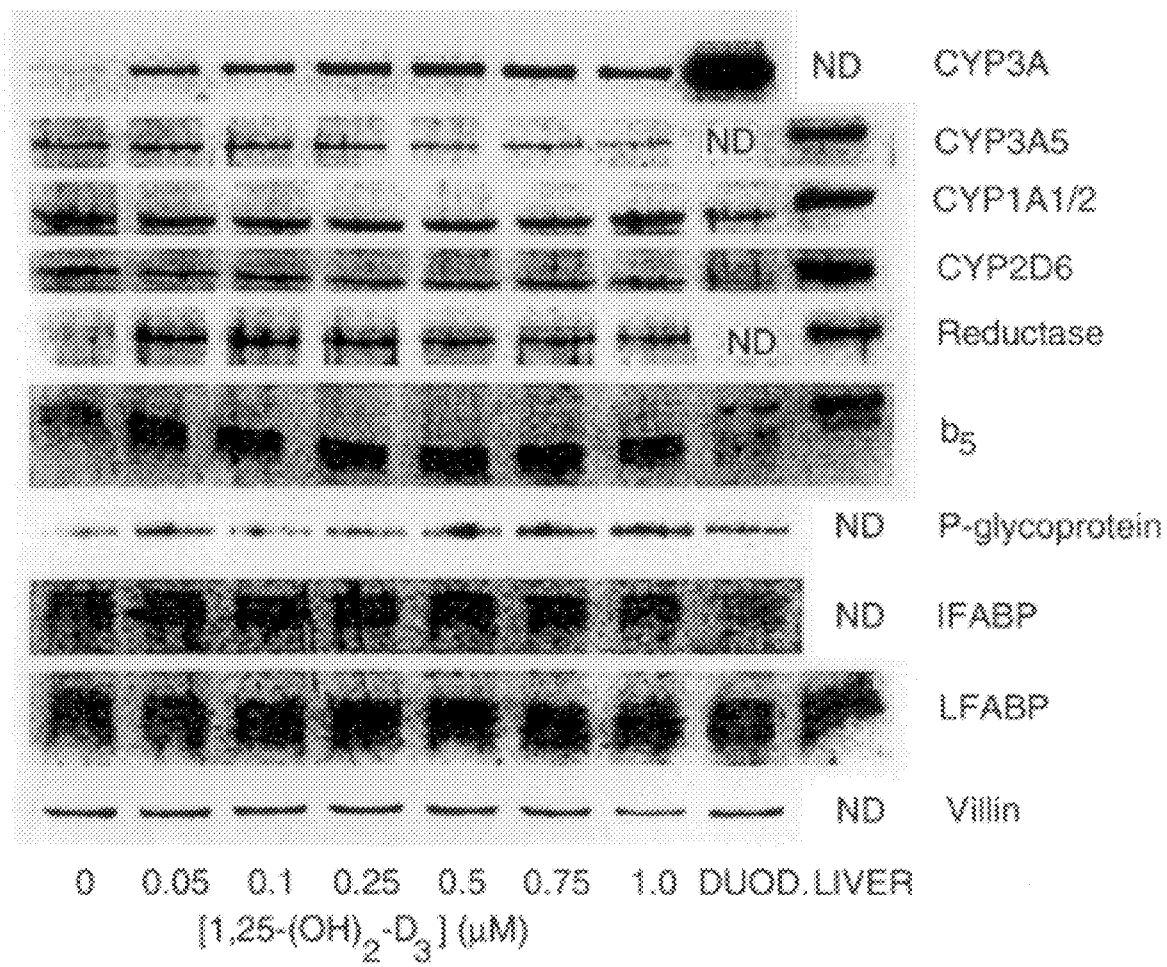
FIG. 3 depicts immunoblots of Caco-2 cell levels of expression of CYP3A, CYP3A5, CYP1A1, CYP2D6, cytochrome P450 reductase, cytochrome $b_5$, P-glycoprotein, IFABP, LFABP, and villin in response to treatment with varying doses of $1\alpha,25\text{-(OH)-}D_3$.

FIG. 3 depicts immunoblots of Caco-2 cell levels of expression of CYP3A, CYP3A5, CYP1A1, CYP2D6, cytochrome P450 reductase, cytochrome $b_5$, P-glycoprotein, IFABP, LFABP, and villin. Each $1\alpha,25$-$(OH)_2$-$D_3$ concentration represents one culture. Of note, these are the same $1\alpha,25$-$(OH)_2$-$D_3$-treated cultures as used for catalytic activity and immunoblotting in the preceding example (see FIG. 2). In FIG. 3, "ND"=not done. Immunoblots showing protein expression in response to 25-(OH)-$D_3$ are not shown.

Immunoblots showed little change in the level of CYP3A5 in response to $1\alpha,25$-$(OH)_2$-$D_3$ (FIG. 3) or to 25-(OH)-$D_3$ (not shown). Levels of CYP3A7 could not be assessed since a specific antibody is not available. Levels of CYP1A1 and CYP2D6 did not appear to change in response to $1\alpha,25$-$(OH)_2$-$D_3$ (FIG. 3) or 25-(OH)-$D_3$. The level of NADPH cytochrome P450 reductase appeared to increase in response to concentrations of $1\alpha,25$-$(OH)_2$-$D_3 \geq 0.05$ $\mu$M (FIG. 3) and concentrations of 25-(OH)-$D_3 \geq 0.5$ $\mu$M (not shown).

An antibody to cytochrome $b_5$ recognized a protein on immunoblots whose level of expression did not appear to change in response to either $1\alpha,25$-$(OH)_2$-$D_3$ (FIG. 3) or 25-(OH)-$D_3$; the $b_5$ immunoreactive protein in the Caco-2 cells did not comigrate with the major immunoreactive protein present in adult small bowel and liver, but did comigrate with a smaller immunoreactive protein present in duodenal homogenate but not detected in human liver microsomes (see FIG. 3). Thus, the results do not appear to indicate the expression of intact cytochrome $b_5$, a co-enzyme required for full activity by CYP3A4 in some of the reactions it catalyzes [P. L. Holmans et al., Arch. Biochem. Biophys. 312:554–565 (1994)]. The possible lack of expression of intact cytochrome $b_5$ might mean that the present model does not precisely mirror the in vivo conditions.

Though an understanding of why intact cytochrome $b_5$ was not detected is not required to practice the present invention, proteolytic degradation during cell processing is unlikely to account for the smaller immunoreactive protein, since the other proteins examined did not appear to be degraded. Additionally, as indicated above, the immunoreactive protein was found to comigrate on polyacrylamide gels with a minor band detected in human small bowel but not liver (FIG. 3). This may possibly represent the soluble form of cytochrome $b_5$ which lacks the membrane anchoring domain [P. L. Holmans et al., Arch. Biochem. Biophys. 312:554–565 (1994)]. The absence of fully-functional cytochrome $b_5$ in the Caco-2 cell model of the present invention may also be suggested by a comparison of cell culture and intestinal mucosal CYP3A content and MDZ 1'-hydroxylation activities. The specific CYP3A content in Caco-2 cell cultures was higher than the mean CYP3A content in duodenal and jejunal mucosal homogenate (20.6 pmol/mg Caco-2 cell protein vs. 9.2 and 8.4 pmol/mg duodenal and jejunal homogenate protein), whereas, the mean intrinsic 1'-OH MDZ formation clearance for Caco-2 cells was only 30% and 31% of the intrinsic formation clearances for duodenal and jejunal mucosae (1.14 mL/min/g Caco-2 cells vs. 3.83 and 3.67 mL/min/g mucosa).

The effect of $1\alpha,25$-$(OH)_2$-$D_3$ and 25-(OH)-$D_3$ on the expression of P-glycoprotein was examined since many substrates of this transport protein are also CYP3A4 substrates [see, e.g., V. J. Wacher et al, Mol. Carcinog. 13:129–134 (1995)]. As indicated in FIG. 3, $1\alpha,25$-$(OH)_2$-$D_3$ and 25-(OH)-$D_3$ (not shown) resulted in increased levels of immunoreactive P-glycoprotein at concentrations $\geq 0.5$ $\mu$M and $\geq 2.5$ $\mu$M respectively. The increase in P-glycoprotein expression may be by a post-transcriptional mechanism since no change in mRNA levels was detected (see FIG. 1).

The responses of IFABP, LFABP, and villin expression to $1\alpha,25$-$(OH)_2$-$D_3$ and 25-(OH)-$D_3$ were examined as controls. Neither of the FABPs showed changes in levels of expression on immunoblots in response to $1\alpha,25$-$(OH)_2$-$D_3$ (FIG. 3) or 25-(OH)-$D_3$ (not shown). Levels of villin immunoreactive protein appeared to decrease slightly in response to 1 $\mu$M $1\alpha,25$-$(OH)_2$-$D_3$ (FIG. 3) or concentrations of 25-(OH)-$D_3 \geq 10$ $\mu$M (not shown).

The top strip in FIG. 3 relates to CYP3A expression. Quantitation of the CYP3A immunoreactive bands in the upper strip by computer aided densitometry, using second loaded serial dilutions of purified CYP3A4 protein, revealed that the band from untreated cells (lane 1) corresponded to 7.9 pmol CYP3A/mg of total protein while the band from cells treated with 0.5 $\mu$M $1\alpha,25$-$(OH)_2$-$D_3$ (lane 5) corresponded to 20.6 pmol CYP3A/mg of total protein. Based on these results, visual interpretation of immunoblots developed with ECL may over-estimate fold increases in levels of expression.

EXAMPLE 6

Electron Micrograph Studies

Some of the previous examples were directed at defining those conditions necessary for optimal expression of CYP3A4. This example addresses whether those conditions resulted in a general increase in differentiation.

Preparation Of Media For Transmission Electron Microscopy

Caco-2 cells grown in the presence or absence of Matrigel and with or without a two-week exposure to 0.25 $\mu$M $1\alpha,25\text{-(OH)}_2\text{-D}_3$ were prepared as described above. In order to prepare sections for electron microscopy, the medium was aspirated and the inserts were washed three times with Hanks' BSS. The monolayers were fixed in 2% glutaraldehyde/4% tannic acid in cacodylate buffer, post-fixed in 1% osmium tetroxide in cacodylate buffer, dehydrated in a graded series of ethanol, and embedded in EPON resin. Sections (70 nm thick) were prepared, post-stained sequentially with 4% uranyl acetate and Reynolds lead citrate, and examined in a Philips Electronics Instruments model CM-10 transmission electron microscope.

Figure 4:
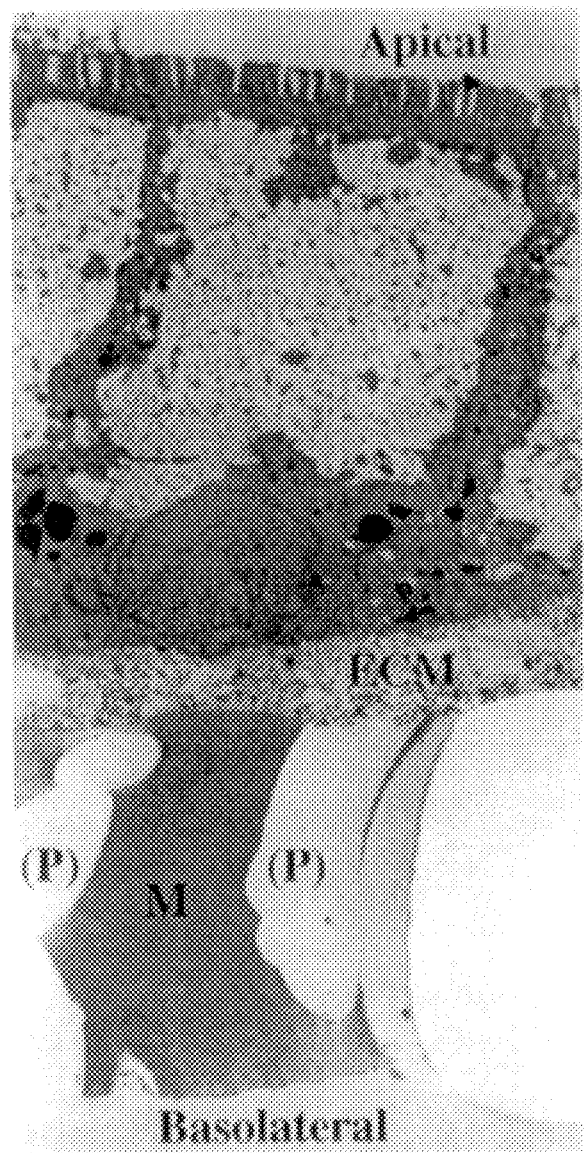
FIG. 4 is a representative electron micrograph of Caco-2 cells grown on a Matrigel-coated polycarbonate culture insert and treated with 0.25 μM $1\alpha,25\text{-(OH)}_2\text{-}D_3$ for two weeks beginning at the time of confluence.

FIG. 4 is a representative electron micrograph of Caco-2 cells grown on a Matrigel-coated polycarbonate culture insert and treated with 0.25 $\mu$M $1\alpha,25\text{-(OH)}_2\text{-D}_3$ for two weeks beginning at the time of confluence. The following abbreviations are used in FIG. 4: Apical, apical compartment; ECM, Matrigel extracellular matrix; M, insert membrane; (P), pore; Basolateral, basolateral compartment. Magnification was at ×905.

Micrograph Analysis

When the electron micrographs were analyzed by an experienced observer blinded to the treatments, no ultrastructural differences indicating differing degrees of differentiation were detected. Moreover, measurements of cell height (~16.5 $\mu$m) and microvillar height (~1.02 $\mu$m) were not clearly affected by the presence or absence of vitamin D or Matrigel. Of note, the microvillar height was less than that reported by Halline et al. [Endocrinology 134:1710–1717 (1994)] (1.52 $\mu$m) for Caco-2 cells grown on plastic and treated with 0.1 $\mu$M $1\alpha,25\text{-(OH)}_2\text{-D}_3$ in medium containing 20% FBS.

EXAMPLE 7

The Effect of the Duration of Exposure to $1\alpha,25\text{-(OH)}_2\text{-D}_3$ This example is directed at the effect of cell culture exposure time to $1\alpha,25\text{-(OH)}_2\text{-D}_3$ on protein expression and catalytic activity.

The Effect of Duration of Exposure on Protein Expression

An assessment was made to determine whether the duration of exposure to $1\alpha,25\text{-(OH)}_2\text{-D}_3$ could be shortened without diminishing the expression of CYP3A. Caco-2 cells were grown on Matrigel-coated teflon culture inserts and were treated with 0.25 $\mu$M $1\alpha,25\text{-(OH)}_2\text{-D}_3$ for varying periods. All cultures tested were of the same age (two weeks post-confluence) at the time of harvesting. More specifically, upon reaching confluence, the medium in all cultures was changed from growth medium containing 20% FBS to differentiation medium containing 5% FBS; 0.25 $\mu$M $1\alpha,25\text{-(OH)}_2\text{-D}_3$ was added at different times post-confluence and continued until the cells of each particular culture were two weeks post-confluence.

At that time, the medium was replaced with medium without vitamin D (except that contributed by the 5% FBS. Total RNA was then prepared as described above and subjected to RT-PCR using synthetic oligonucleotide primer pairs designed to selectively amplify fragments of the CYP3A4 and villin cDNAs (see Table 3). The numbers of PCR cycles were as follows: CYP3A4, 36; and villin, 27. Moreover, immunoblots were performed as described above for CYP3A, NADPH cytochrome P450 reductase, P-glycoprotein, and villin. The protein loads used for the immunoblot procedures were as follows: 5 $\mu$g for CYP3A, P-glycoprotein, villin; and 40 $\mu$g for NADPH cytochrome P450 reductase.

FIG. 5A depicts an ethidium bromide stained agarose gel (top panel labeled "PCR") and an immunoblot (bottom panel labeled "Immunoblot") indicating the duration of exposure to $1\alpha,25\text{-(OH)}_2\text{-D}_3$ necessary to achieve increased expression of CYP3A4 mRNA and CYP3A4, NADPH cytochrome P450 reductase, and P-glycoprotein immunoreactive proteins. Each time point represents two different cultures, one used for mRNA analysis by RT-PCR and another used for immunoblots of cell homogenates and catalytic activity. As set forth in the top panel of FIG. 5A, an increase in CYP3A4 mRNA was evident after 3–4 hours of exposure to 0.25 $\mu$M $1\alpha,25\text{-(OH)}_2$-D3, and when band density on ethidium stained gels was measured by computer aided densitometry, appeared to plateau at 120 hours (5 days) of exposure to $1\alpha,25\text{-(OH)}_2\text{-D}_3$.

As indicated in the bottom panel of FIG. 5A, increased CYP3A protein expression became evident on the immunoblots at 18 hours and continued to rise throughout the remainder of the two-week experiment. Immunoreactive NADPH cytochrome P450 reductase did not appear to increase until 168 hours (7 days) of exposure to $1\alpha,25\text{-(OH)}2\text{-D}_3$; its increased expression may be in response to another induced protein, perhaps CYP3A4, rather than in direct response to $1\alpha,25\text{-(OH)}_2\text{-D}_3$. Immunoreactive P-glycoprotein appeared to increase beginning at about 72 hours of exposure to $1\alpha,25\text{-(OH)}_2\text{-D}_3$. Finally, the levels of villin mRNA and immunoreactive protein did not appear to change over the two week course of the experiment (FIG. 5A, top and bottom panels, respectively).

The Effect of Duration of Exposure on Catalytic Activity

In order to determine the rate of CYP3A catalytic activity, midazolam metabolism was measured. As previously indicated, the medium was aspirated and the inserts were washed three times with Hanks'BSS. Next, 1.5 mL of fresh complete differentiation medium was placed on each side of the insert, with 4 $\mu$M midazolam present in the medium placed on only one side of the monolayer (the apical medium). The incubation media did not contain vitamin D (except that contributed by the 5% FBS). After 6 hours, the amount of 1'-OH-MDZ was measured in the combined luminal plus basolateral medium from each culture and the rate of formation calculated.

Figure 5B:
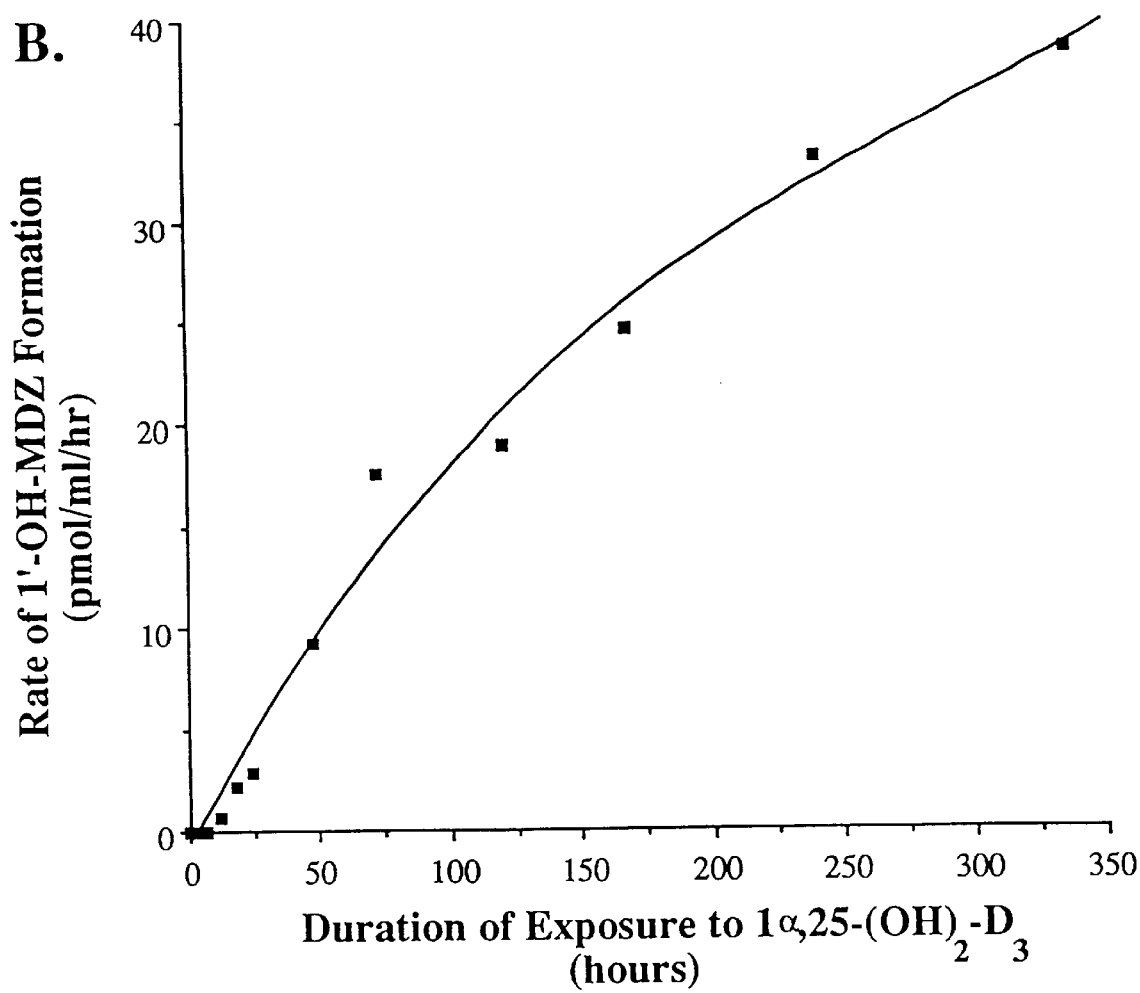
FIG. 5B graphically illustrates the rate of CYP3A catalytic activity (as assessed by the rate of 1'-OH-MDZ formation) by Caco-2 cells as a function of the duration of exposure to $1\alpha,25\text{-(OH)}_2\text{-}D_3$.

FIG. 5B graphically illustrates the rate of CYP3A catalytic activity (as assessed by the rate of 1'-OH-MDZ formation) by Caco-2 cells as a function of the duration of exposure to $1\alpha,25\text{-}(OH)_2\text{-}D_3$. As indicated by FIG. 5B, midazolam metabolism showed a pattern similar to that for CYP3A expression, first becoming detectable in cultures exposed to $1\alpha,25\text{-}(OH)_2\text{-}D_3$ for 12 hours and continuing to rise throughout the remainder of the two-week experiment.

Of note, exposure to $1\alpha,25\text{-}(OH)_2\text{-}D_3$ resulted in far greater increases in CYP3A4 catalytic activity (>50-fold, FIGS. 2A and 5B) than in CYP3A immunoreactive protein (~3 fold). Though an understanding of this effect is not required to practice the present invention, these results suggest that the CYP3A enzymes present in untreated cells are largely inactive, and that factors other than the increase in CYP3A protein contribute to the increases in catalytic activity we observed. One important factor may be the increase in NADPH cytochrome P450 reductase which was also observed during treatment (see FIGS. 3 and 7). However, it is unlikely that the increase in this essential cofactor alone is responsible, because the rapid rise in catalytic activity (FIG. 5B) appears to occur prior to the increase in reductase protein (FIG. 5A). Other processes essential for optimal catalytic activity (such as heme incorporation into apoprotein) may also be improved by the culture conditions of the present invention.

EXAMPLE 8

The Effect Of Verapamil on $1\alpha,25\text{-}(OH)_2\text{-}D_3$ Catalytic Activity This example describes the effect over time of midazolam metabolism in Caco-2 cells treated with $1\alpha,25\text{-}(OH)_2\text{-}D_3$ in the presence and absence of verapamil. Verapamil is a substrate of CYP3A4 and an inhibitor of P-glycoprotein.

The Effect of Verapamil on MDZ Metabolism

Caco-2 cells were grown on Matrigel-coated teflon culture inserts and treated with 0.25 $\mu$M $1\alpha,25\text{-}(OH)_2\text{-}D_3$ for two weeks beginning at the time of confluence. At the end of this period, the medium was replaced with medium not containing vitamin D (except that contributed by the 5% FBS). Next, 4 $\mu$M MDZ was added to the apical (luminal) or basolateral (serosal) medium of the cells. In selected cultures, 100 $\mu$M verapamil, a P-glycoprotein inhibitor was applied apically. After incubation for 0–24 hours, the apical and basolateral media were removed separately and analyzed for concentrations of 1'-OH-MDZ and MDZ.

Figure 6A:
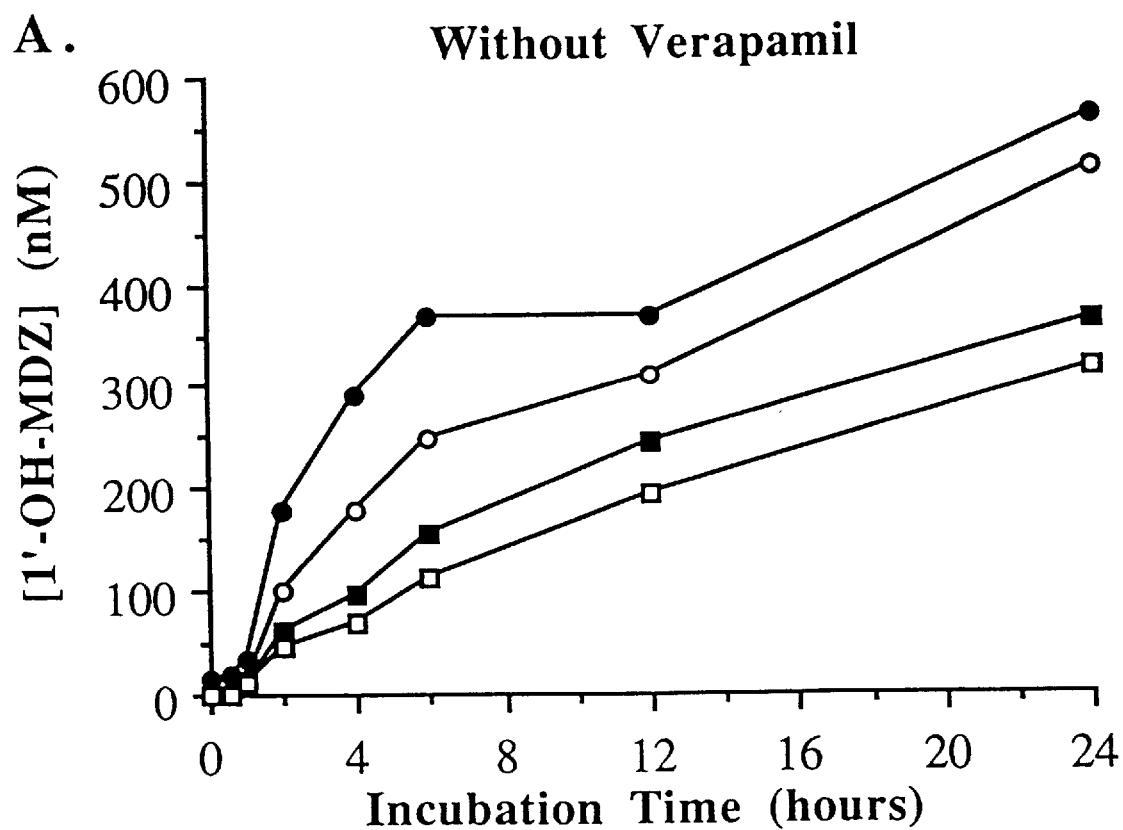
FIGS. 6A–D graphically depict the time course of MDZ metabolism by Caco-2 cells treated with $1\alpha,25\text{-(OH)}_2\text{-}D_3$ alone (FIGS. 6A and B) or with $1\alpha,25\text{-(OH)}_2\text{-}D_3$ and verapamil (FIGS. 6C and D).
Figure 6B:
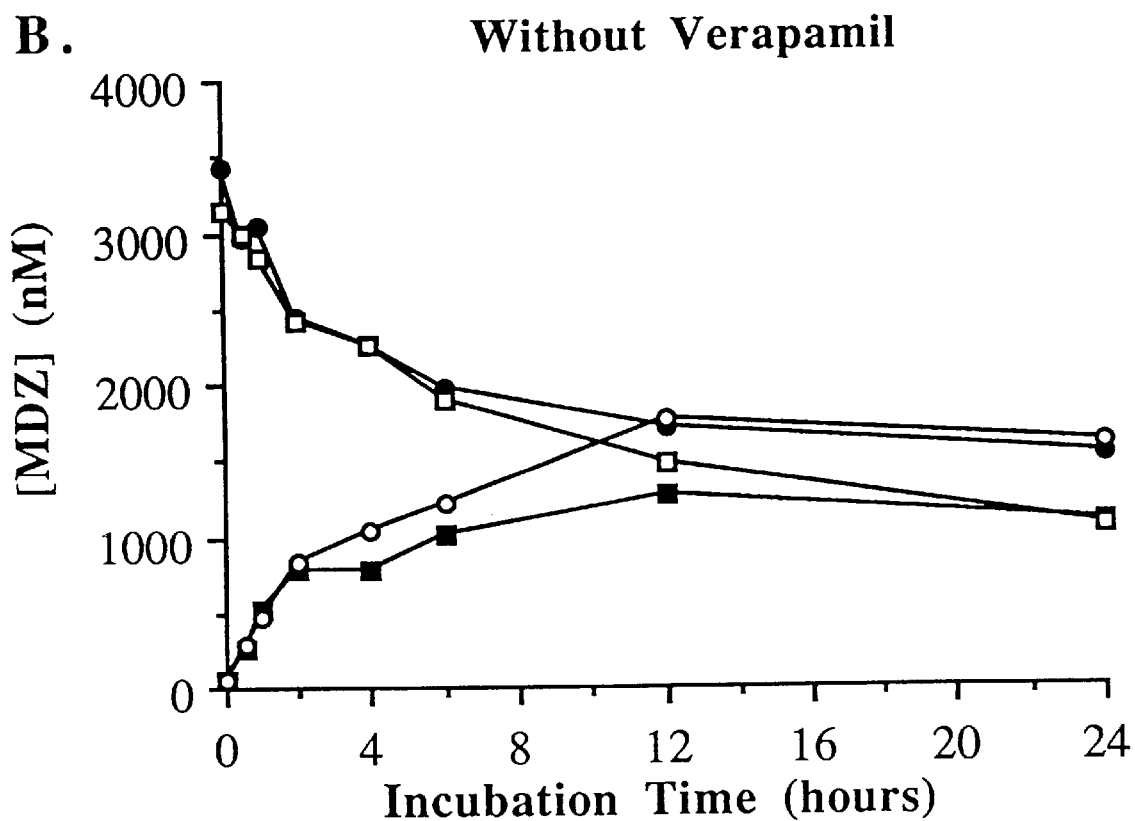
Figure 6C:
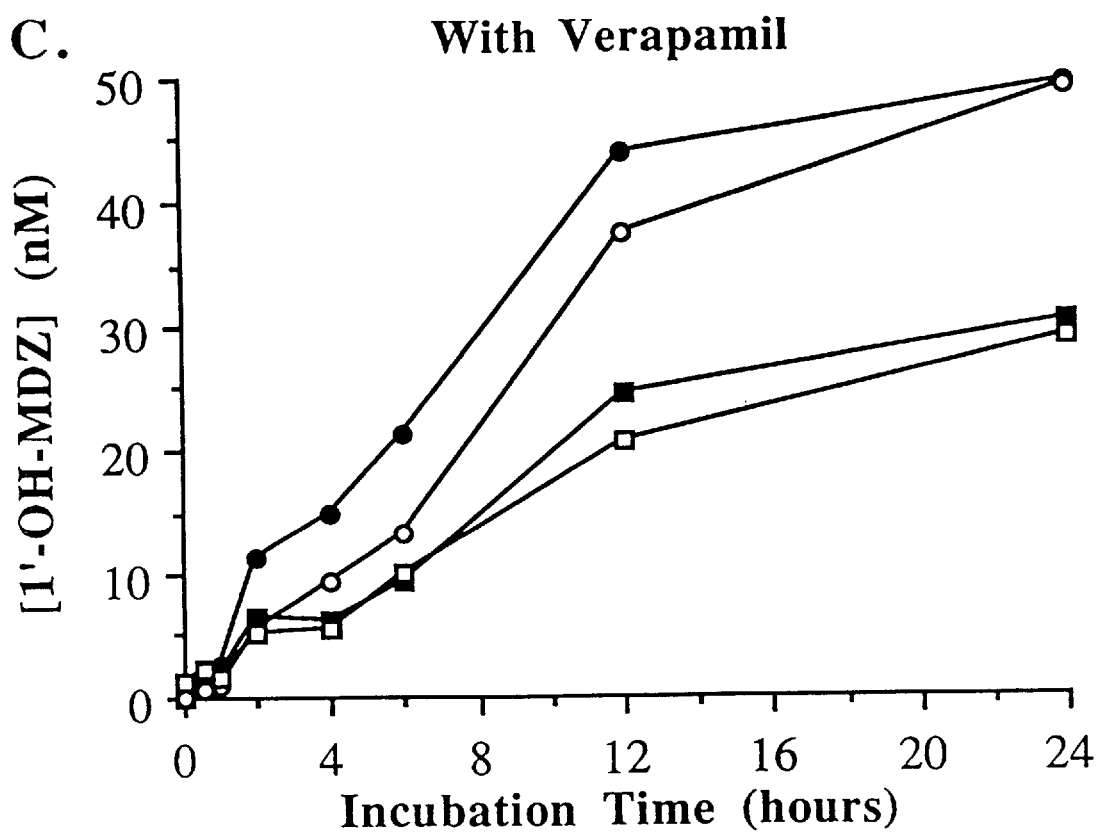

FIGS. 6A–D graphically depict the time course of MDZ metabolism by Caco-2 cells treated with $1\alpha,25\text{-}(OH)_2\text{-}D_3$ alone (FIGS. 6A and B) or with $1\alpha,25\text{-}(OH)_2\text{-}D_3$ and verapamil (FIGS. 6C and D). Each point on FIGS. 6A and 6C represents metabolite (1'-OH-MDZ) data from a separate culture, with the corresponding parent compound (MDZ) data on FIGS. 6B and 6D. It should be noted that FIGS. 6A and 6C entail different scales for the concentration of 1'-OH-MDZ formed. In FIGS. 6A–D, the shaded circles represent apical media following apical administration of MDZ, the shaded squares represent basolateral medium following apical administration of MDZ, the open circles represent apical medium following basolateral administration of MDZ, and the open squares represent basolateral medium following basolateral administration of MDZ.

As indicated in FIG. 6A, 1'-OH-MDZ became detectable by 1 hour after MDZ administration to either compartment. The rate of 1'-OH-MDZ formation appeared to slow slightly over time, but remained roughly constant after 6 hours. At every time point, the concentration of 1'-OH-MDZ was greater in the apical medium than in the basolateral medium, even when MDZ had been administered basolaterally. Referring to FIG. 6B, the apical concentration of parent compound following apical administration declined over the first 12 hours, but a stable, approximately 1.4-fold apical-to-basolateral concentration gradient was then maintained for the remainder of the 24 hours. By 12 hours, the parent compound had also distributed preferentially to the apical medium after basolateral administration.

Because many substrates for CYP3A4 are also believed to be substrates for P-glycoprotein, it appeared feasible that P-glycoprotein might be responsible for the observed concentration gradients. However, as verapamil had no detectable effect on the concentration gradients generated for either parent compound or metabolite, it appears that P-glycoprotein may not be involved. Secretory efflux of xenobiotics not mediated by P-glycoprotein has been shown to occur in Caco-2 cells [G. K. Collington et al., Biochem. Pharmacol. 44:417–424 (1992)].

Figure 6D:
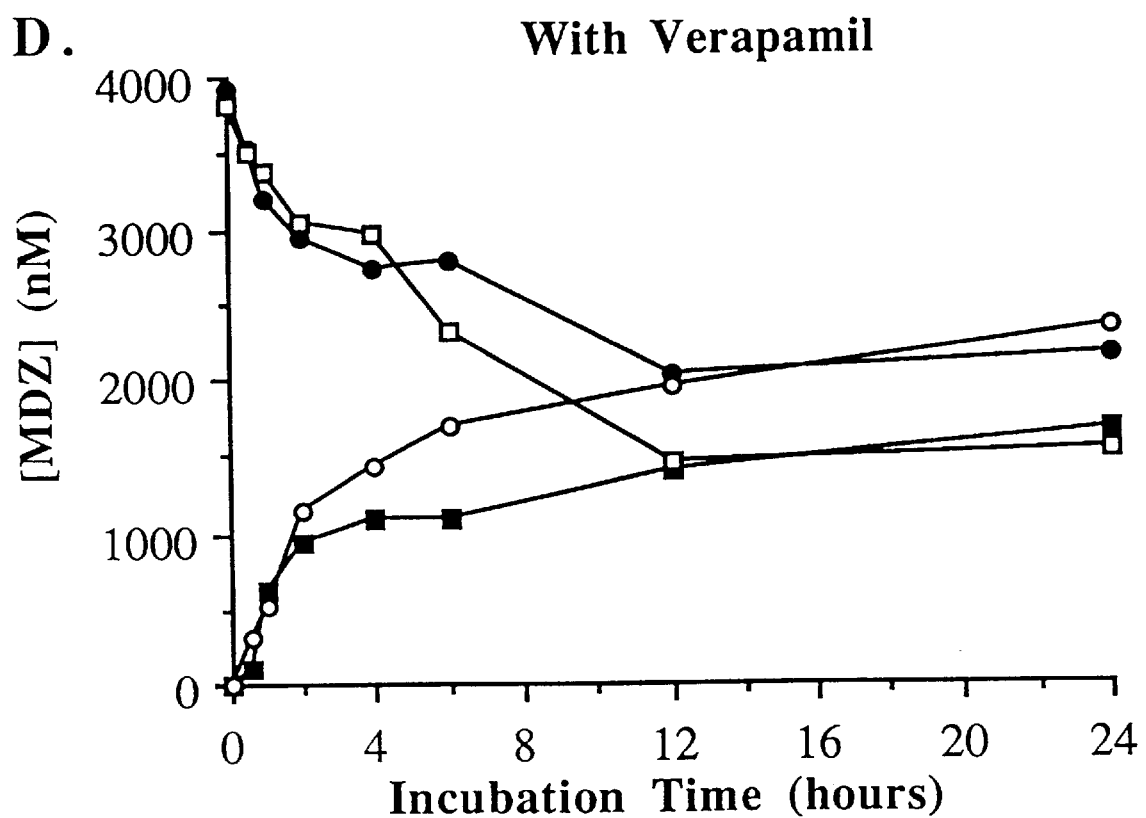

The effect of verapamil administration to the apical compartment during MDZ metabolism time courses is set forth in FIGS. 6C and 6D. In contrast to the lack of change in concentration gradients, comparison of FIGS. 6C with 6A reveals that verapamil administration resulted in an approximately 90% inhibition of 1'-OH-MDZ formation. As verapamil is a substrate for CYP3A4, the decreased metabolism observed likely resulted from competitive inhibition of the enzyme ($K_i$ of 23.5 $\mu$M determined in cultured hepatocytes) [L. Pichard et al., Drug Metab. Dispos. 18:595–606 (1990)]. However, the apical-to-basolateral concentration gradients of both parent MDZ (FIG. 6D) and the 1'-OH metabolite (FIG. 6C) were similar to those observed in the absence of verapamil (see FIGS. 6B and 6A, respectively).

The experiments with midazolam demonstrate that selective inhibitors can be used in the culture system of the present invention to define the roles of transporters and CYP3A4 in determining the oral bioavailability of xenobiotics. In addition, by varying the concentration and duration of exposure to $1\alpha,25\text{-}(OH)_2\text{-}D_3$, one can vary the activity of CYP3A4 in the culture system. This may be important, for example, for the study of substrates of both CYP3A4 and P-glycoprotein, where inhibitors known to act on one but not the other are unavailable.

EXAMPLE 9

Glucuronidation Of 1'-OH-MDZ

The glucuronide of 1'-OH-MDZ is a major metabolite found in the blood and urine of patients given midazolam intravenously or orally. However, it has recently been demonstrated that midazolam glucuronidation occurs primarily in the liver and not in the intestine in vivo [M. F. Paine et al., Clin. Phamacol. Ther. 59:491–502 (1996)]. The experiments of this example assess whether glucuronidation occurs in the culture system of the present invention. To determine whether the glucuronide conjugate of 1'-OH-MDZ was formed during Caco-2 cell incubations, 0.5 mL aliquots of apical and basolateral culture medium from cells incubated for 2–24 hours with 4 $\mu$M MDZ (administered apically) were added to 0.5 mL 100 mM sodium acetate, pH 5.0, containing 200 units β-glucuronidase. Samples were spiked with 20 ng 1'-[$^2$H$_2$],1'-OH-MDZ and incubated at 37° C. for 24 hours. Each of a complete set of parallel 0.5 mL samples was diluted to a volume of 1 mL and spiked with 20 ng 1'-[$^2$H$_2$],1'-OH-MDZ (no glucuronidase treatment). To both sets of samples was added 1 mL 50 mM NaCO$_3$, pH 12.5;

all were then processed as described above and quantitated for total (conjugated plus unconjugated) and unconjugated 1'-OH-MDZ concentration by mass spectrometry.

There were no differences between the 1'-OH-MDZ concentrations obtained after glucuronidase treatment (not shown) as compared to the concentrations obtained without hydrolysis, indicating that glucuronidation of 1'-OH-MDZ had not occurred in the Caco-2 cells. This result is expected because, as indicated above, glucuronidation occurs in the liver and not in the intestine.

EXAMPLE 10

Intrinsic 1'-OH-MDZ Clearance

Based on the data obtained from the time course experiments in the preceding example, the intrinsic 1'-OH-MDZ formation clearance was calculated for Caco-2 cells. That clearance was then compared to the intrinsic 1'-OH-MDZ clearance determined for human duodenal and jejunal mucosa.

Calculation of an Intrinsic 1'-OH-MDZ Clearance for Cultured Caco-2 Cells

Intrinsic 1'-OH-MDZ formation clearance was calculated from the 24-hour time course data obtained in the cultures dosed apically with MDZ (4 $\mu$M) in the absence of verapamil. Parent drug and metabolite concentrations measured at 1 and 2 hours after MDZ administration were used for computation. The amount of 1'-OH-MDZ formed during this interval was determined as the sum of metabolite in the apical and basolateral compartments at 2 hours minus the total amount measured at 1 hour. The rate of product formation was normalized for the total mass of Caco-2 cells in each culture insert (an average of 65 mg), measured at the end of the MDZ incubation period (following Dispase digestion, washing, and centrifugation of the cells).

Because the incubation medium contained significant amounts of FBS, the fraction of MDZ bound to culture medium proteins was measured by equilibrium dialysis. The fraction of MDZ bound to culture medium proteins was dialyzed against sodium phosphate buffer (about 1 mL of 67 mmol/L), pH 7.4, at 37° C. for approximately four hours [K. E. Thummel et al., Clin. Pharmacol. Ther. 59:491–502 (1996)]. The unbound concentration of MDZ in the apical and basolateral compartments during cell culture was calculated as the product of the experimentally determined MDZ-free fraction and total MDZ concentration. Since MDZ concentrations in the apical and basolateral compartments were not at equilibrium during the 1–2 hour MDZ incubation interval, the intracellular reaction was assumed to be driven by a MDZ concentration that was more closely aligned with the concentration in the basolateral compartment. Thus, the intrinsic 1'-OH-MDZ formation clearance (assuming sub-saturating MDZ concentrations) was calculated as the ratio of the 1'-OH-MDZ formation rate and the average (1–2 hour) unbound MDZ concentration in the basolateral compartment. It should be noted that this calculation assumes that any potential MDZ transport mechanism is located in the apical membrane.

Table 4 sets forth the MDZ-1'-OH kinetics in Caco-2 cell cultures at the 1–2 h incubation interval.

TABLE 4

Midazolam 1'-Hydroxylation Kinetics in Caco-2 Cell Cultures at the 1–2 h Incubation Interval.

| | |
|---|---|
| 1'-Hydroxymidazolam Formation Rate | 75.9 pmol/min/g cells |
| Average Midazolam Concentration | |
| Basolateral | 650 nM |
| Apical | 2740 nM |
| Unbound Midazolam Concentration | |
| Basolateral | 66.3 nM |
| Apical | 280 nM |
| Intrinsic Formation Clearance | 1.14 ml/min/g cells |

As indicated in Table 4, the rate of 1'-OH-MDZ formation was found to be 75.9 pmol/min/g cells. Under equilibrium dialysis conditions, approximately 89.8% of MDZ was found to be bound to medium proteins, yielding an unbound fraction of 10.2% (as determined by the calculations described above). Thus, the total and unbound MDZ concentration in the basolateral compartment was estimated to be 650 nM and 66.3 nM, respectively. The intrinsic 1'-OH-MDZ formation clearance under non-saturating conditions ($K_m \sim 3.4$ $\mu$M, [see K. E. Thummel et al., Clin. Pharmacol. Ther. 59:491–502 (1996)]) was estimated to be 1.14 mL/min/g cells.

Calculation of an Intrinsic 1'-OH-MDZ Clearance for Human Duodenal and Jejunal Mucosa For comparison, an intrinsic 1'-OH-MDZ formation clearance was determined for eight paired human duodenal and jejunal mucosae. The mucosal mass was removed from ~1 foot sections of duodenum and jejunum and total homogenate and microsomes were prepared, as described above. Two of eight preparations contained relatively low amounts of CYP3A5 in addition to CYP3A4, which were resolved from one another by SDS-PAGE. Microsomes were incubated with varying concentrations of MDZ for determination of $K_m$ and $V_{max}$ parameters for 1'-hydroxylation. Protein concentrations for homogenate and microsomes were measured by the Lowry et al. method [J. Biol. Chem. 193:265–275 (1951)]. The specific CYP3A4 content (pmol/mg protein) in homogenate and microsomes was measured by immunoblot analysis [E. D. Kharasch and K. E. Thummel, Anesth. Analg. 76:1033–1039 (1993)].

The total amount of microsomal protein per gram of mucosa was determined from the following relationship:

$$\frac{\text{mg microsomal protein}}{\text{g mucosa}} = \frac{\text{mg homogenate protein}}{\text{g muscosa}} \times \frac{\text{mg microsomal protein}}{\text{mg homogenate protein}}$$

$$\text{where } \frac{\text{mg microsomal protein}}{\text{mg homogenate protein}} = \frac{(\text{pmol } CYP3A4/\text{mg homogenate protein})}{(\text{pmol } CYP3A4/\text{mg microsomal protein})}$$

This calculation assumes that CYP3A4 found in mucosal homogenate resides exclusively within the microsomal fraction. The microsomal intrinsic formation clearance was calculated as the ratio of $V_{max}$ to $K_m$. The intrinsic 1'-OH-MDZ formation clearance per gram of mucosa was calculated as the product of the microsomal intrinsic formation clearance and the computed amount of microsomal protein per gram of mucosa.

TABLE 5

CYP3A content and midazolam hydroxylation activity in human duodenum and jejunum.

|  | Duodenum | Jejunum |
|---|---|---|
| Microsomal CYP3A (pmol/mg protein) | 41.3 ± 30.5 | 39.7 ± 31.2 |
| Microsomal Intrinsic Clearance (μL/min/mg protein) | 133.8 ± 109.1 | 118.3 ± 98.2 |
| Homogenate CYP3A (pmol/mg protein) | 9.2 ± 6.2 | 8.4 ± 5.4 |
| Mucosal CYP3A (nmol/g mucosa) | 0.89 ± 0.58 | 0.91 ± 0.61 |
| Mucosal Intrinsic Clearance (ml/min/g mucosa) | 3.83 ± 3.62 | 3.67 ± 3.81 |

As indicated in Table 5, the mean intrinsic 1'-OH-MDZ formation clearance for eight different human duodenal and jejunal microsomes was found to be 133.8 and 118.3 μL/min/mg protein, respectively. Values for each section of intestine were quite variable, with an interindividual variation of 15-fold and 20-fold for duodenum and jejunum, respectively. The average microsomal protein content (±SD) in duodenal and jejunal mucosa was found to be 25.4±14.4 and 27.7±18.7 mg protein/g mucosa, respectively.

Through the use of densitometric quantitation and serial dilutions of purified CYP3A4 which had been second loaded on the gel (described above in relation to FIG. 2C) for construction of a standard curve, it was determined that untreated Caco-2 cells contained approximately 7.9 pmol of total CYP3A/mg of protein while the maximal expression (at 0.5 μM 1α,25-(OH)$_2$-D$_3$) corresponded to 20.6 pmol of total CYP3A/mg of cell protein. For comparison, the mean (±SD) CYP3A4 content in mucosal homogenates prepared from human duodenum and jejunum was found to be 9.2±6.2 and 8.4±5.4 pmol/mg protein, respectively (see Table 5).

As indicated by the data set forth above, the intrinsic 1'-OH-MDZ formation clearance for 1α,25-(OH)$_2$-D$_3$ pretreated Caco-2 cells compared well to human intestinal mucosa, representing 30% and 31% of the mean intrinsic formation clearance determined for human duodenal and jejunal mucosa, respectively.

EXAMPLE 11

Measurement Of 1'-OH-MDZ/4-OH-MDZ Product Formation Ratio

This example compares 1'-OH-MDZ/4-OH-MDZ product formation ratios calculated for selected Caco-2 cells and for human jejunal microsomes.

All CYP3A isoforms catalyze both the 1'- and 4-hydroxylation of midazolam. However, different 1'-OH-MDZ/4-OH-MDZ product ratios are produced by the three known human CYP3A isoforms (CYP3A4, CYP3A5, and CYP3A7). For CYP3A4, metabolism of MDZ at the 1'-position predominates, although hydroxylation at the 4-position is increasingly favored with increasing MDZ concentrations [J. C. Gorski et al., Biochem Pharmacol. 47:1643–1653 (1994)].

Product Ratios with Cultured Caco-2 Cells

As part of the CYP3A isoform characterization, the 1'-OH-MDZ/4-OH-MDZ product formation ratio was measured in selected Caco-2 cell cultures. More specifically, product formation ratios were determined for clone 5 (which maximally expresses CYP3A immunoreactive protein, whether treated or untreated with 1α,25-(OH)$_2$-D$_3$) and clone 7 (which was used for all of the other experiments described in the Experimental section).

The minor CYP3A4 metabolite, 4-OH-MDZ, was quantitated along with 1'-OH-MDZ following incubations with 4 μM midazolam added to the apical medium. For the assay, base-treated culture medium was spiked with $^{15}$N$_3$-1'-OH-MDZ and $^{15}$N$_3$-4-OH-MDZ (~50 ng/10 ng fixed ratio) and processed as described above.

Standard curves for both 1'-OH-MDZ (1–50 ng) and 4-OH-MDZ (0.5–25 ng) were also prepared. The only modifications to the mass spectrometric assay involved monitoring molecular ions with m/z 455 and 460 (for unlabeled and $^{15}$N$_3$-labeled $^{37}$Cl isotope of 1'-OH-MDZ, respectively) and base peak fragment ions ([M-tBu (CH$_3$)$_2$SiOH]$^-$) with m/z 323 and 328 (for unlabeled and $^{15}$N$_3$-labeled $^{37}$Cl isotope of 4-OH-MDZ, respectively). 4-OH-MDZ exhibited a slightly shorter GC column retention time than 1'-OH-MDZ (12.7 vs. 14.0 min), under defined GC conditions [M. Paine et al., Clin. Pharmacol. Ther. 60:14–24 (1996)].

Table 6 sets forth the 1'-Hydroxymidazolam/4-hydroxymidazolam formation ratios from incubations of midazolam with cultured Caco-2 cells from clone 5 and clone 7 (ND, not done).

TABLE 6

1'-Hydroxymidazolam/4-hydroxymidazolam formation ratios from incubations of midazolam with cultured Caco-2 Cells.

| Cells | Duration of 1a,25-(OH)$_2$-D$_3$ Treatment | Extracellular Matrix | Duration of Midazolam Incubation | 1'-OH-MDZ/4-OH-MDZ Apical | Basolateral |
|---|---|---|---|---|---|
| Clone 5 |  |  |  |  |  |
|  | 336 h | Matrigel | 7.5 h | 5.4 | 5.2 |
|  | untreated | Matrigel | 7.5 h | 4.5 | 3.6 |
| Clone 7 |  |  |  |  |  |
|  | 12 h | Matrigel | 6 h | 3.8 | ND |
|  | 120 h | Matrigel | 6 h | 5.1 | ND |
|  | 336 h | Matrigel | 6 h | 5.3 | ND |
|  | 336 h | Iaminin | 7 h | 5.4 | 5.2 |
|  | 336 h | Matrigel | 7 h | 5.3 | 5.2 |

As indicated by the data presented in Table 6, there was an increase in the product ratio from 3.8 to 5.3 with an increase in duration of treatment (12 h vs. 336 h) with 1α,25-(OH)$_2$-D$_3$. Clone 5 had sufficient metabolic activity for measurements to be made in both the 1α,25-(OH)$_2$-D$_3$ treated and untreated states. In the treated culture, the product ratios were 5.4 and 5.2 for apical and basolateral compartments, respectively, while in the untreated culture the product ratios were slightly lower at 4.5 (apical) and 3.6 (basolateral). In cultures of clone 7, a product formation ratio greater than 5 was obtained in 1α,25-(OH)$_2$-D$_3$ treated cells grown on either laminin or Matrigel.

Product Ratios with Human Jejunal Microsomes

For comparison, 1'-OH/4-OH-MDZ product ratios were also measured in incubations of human jejunal microsomes. Microsomes were prepared from twelve different organ donors and stored at −70° C. The method for obtaining intestinal microsomes has been described [K. E. Thummel et al., Clin. Pharmacol. Ther. 59:491–502 (1996)]. Briefly, the jejunum was removed during organ procurement surgery and frozen on dry ice. Approximately 50–100 g of tissue was thawed in cold normal saline containing 0.1 mmol/L PMSF, pH 7.4. The intestinal sac was opened along the longitudinal axis, and the mucosa was removed by scraping the luminal surface with a glass slide. Next, the mucosal mass (about 10 to 20 mL) was diluted five-fold (v/v) with a buffer solution (10 mmol/L potassium phosphate, pH 7.4, 0.25 mol/L sucrose, 1 mmol/L EDTA, 0.1 mmol/L PMSF) and homogenized. Finally, the microsomal pellet was isolated by differential ultracentrifugation. Protein concentration was determined by the method of O. H. Lowry et al. [J. Biol. Chem. 193:265–275 (1951)], using BSA as a reference standard. Each preparation was analyzed by immunoblotting for CYP3A4 and CYP3A5 content by the procedure described above [see E. D. Kharasch and K. E. Thummel, Anesth. Analg. 76:1033–1039 (1993)]. Six were preselected for determination of the MDZ metabolite ratio, based on the detection of both CYP3A4 and CYP3A5 (n=3), or CYP3A4 only (n=3).

Microsomes (100–200 μg protein) were thawed and suspended, in duplicate, to a volume of 0.9 mL in cold potassium phosphate buffer (0.1M, pH 7.4) containing varying concentrations of MDZ. The final midazolam concentration was set at 0, 0.25, 1, 4, or 8 μM. Incubation mixtures were preincubated in a Dubnoff metabolic shaking incubator at 37° C. for 5 min. The reaction was initiated by the addition of NADPH (1 mM final concentration in 1 mL) and terminated after 4 min by the addition of 1 mL of 0.1M Na$_2$CO$_3$ (final pH ~11). Alkalinized incubation samples were spiked with ~50 ng $^{15}$N$_3$-1'-OH-MDZ and ~10 ng $^{15}$N$_3$-4-OH-MDZ (fixed ratio) and processed for mass spectrometric analysis as described above.

The ratios of 1'-OH-MDZ/4-OH-MDZ for all permutations are presented in Table 7; the "HI" designations in Table 7 identify the human source of the microsomes.

TABLE 7

1'-OH-MDZ/4-OH-MDZ metabolite concentration ratios from incubations of MDZ with human jejunal microsomes.

| | Initial MDZ Concentration (μM) | | | |
|---|---|---|---|---|
| | 0.25 | 1.00 | 4.00 | 8.00 |
| CYP3A4 | | | | |
| HI-19 | 7.4 | 8.1 | 6.8 | 5.6 |
| HI-20 | 9.0 | 8.9 | 7.1 | 5.8 |
| HI-28 | 8.5 | 8.6 | 7.0 | 5.7 |
| CYP3A4 & 3A5 | | | | |
| HI-30 | 15.4 | 12.1 | 12.2 | 9.7 |
| HI-31 | 11.2 | 10.6 | 8.7 | 7.0 |
| HI-35 | 11.1 | 10.3 | 8.3 | 6.7 |

In general, product formation ratios determined for intestinal microsomes were higher than those found in Caco-2 cell cultures. For those intestines that contained only CYP3A4, the 1'-OH-MDZ/4-OH-MDZ ratios varied from 7.4 to 9.0 for incubations with 0.25 μM MDZ and from 5.6 to 5.8 for incubations with 8 μM MDZ. As expected, since CYP3A5 gives a higher product ratio than does CYP3A4 [J. C. Gorski et al., Biochem Pharmacol. 47:1643–1653 (1994)], higher ratios were generated in incubations with intestinal microsomes containing both CYP3A4 and CYP3A5. Values of 11.2 to 15.4 and 6.7 to 9.7 were measured at 0.25 μM and 8 μM MDZ, respectively.

The experiments of this example indicate that product ratios from Caco-2 cell cultures were most similar to those from intestinal microsomes that contained only CYP3A4, although lower than those from intestinal microsome incubations with the most comparable concentrations (0.25–1.0 μM) of MDZ (predicted unbound intracellular concentrations in the Caco-2 cells were ~0.07 μM).

EXAMPLE 12

Comparison Of CYP3A Protein Expression And CYP3A Catalytic Activity In Caco-2 Cell Clones and The Parent Cell Line For the experiments of this example, all cells (Caco-2 cell clones and the parent cell line) were grown on Matrigel-coated teflon culture inserts. One set of cultures was treated with 0.25 μM 1α,25-(OH)$_2$-D$_3$ for two weeks beginning at the time of confluence, while a duplicate set was left untreated. At the end of this period, the medium was replaced with medium not containing vitamin D (except that contributed by the 5% FBS). Next, MDZ (4 μM) was added to the apical compartment. After 7.5 hours, the apical and basolateral media were collected separately. Catalytic activity and levels of protein expression were determined as previously described.

Figure 7:
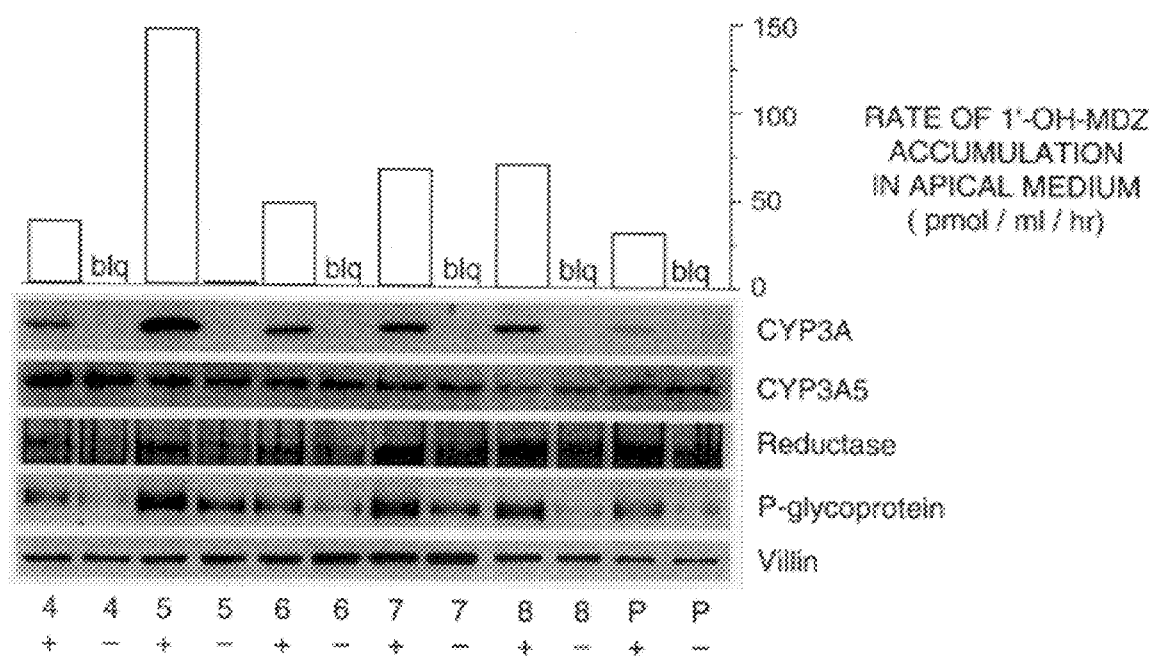
FIG. 7 graphically compares CYP3A catalytic activity in Caco-2 cell clones and the parent cell line (top panel) and depicts immunoblots comparing levels of selected immunoreactive proteins in Caco-2 cell clones and the parent cell line (bottom panel) in the presence and absence of treatment with $1\alpha,25\text{-(OH)}_2\text{-}D_3$.

Referring to FIG. 7, the numbers (4, 5, 6, 7, and 8) along the bottom of FIG. 7B refer to the five cell clones described in Example 1, whereas the "P" designates the parent cell line. The (+) signifies cells treated with 0.25 μM 1α,25-(OH)$_2$-D$_3$, while the (−) signifies cells left untreated (−). These designations apply to both the top and bottom panels of FIG. 7.

The top panel of FIG. 7 graphically illustrates CYP3A catalytic activity, as determined by the rate of 1'-OH-MDZ accumulation in apical medium. As the data indicate, the cells treated with 1α,25-(OH)$_2$-D$_3$ had demonstrably greater catalytic activity than the untreated cells (blq, below limits of quantitation). This was observed for the parent cell line as well as for each clone.

The bottom panel of FIG. 7 depicts immunoblots comparing levels of selected immunoreactive proteins in Caco-2 cell clones and the parent cell line in the presence and absence of treatment with $1\alpha,25\text{-}(OH)_2\text{-}D_3$. The protein loads were as follows: 5 µg for CYP3A, CYP3A5, P-glycoprotein, villin; and 60 µg for NADPH cytochrome P450 reductase. Immunoblots of homogenates of the cells were developed with antibodies of the specificities described above. With longer exposures of the film, a CYP3A band was seen with each of the untreated cells.

The data presented above indicate that all five of the clones as well as the parent cell line showed increased levels of CYP3A immunoreactive protein following two weeks of treatment with 0.25 µM $1\alpha,25\text{-}(OH)_2\text{-}D_3$. The midazolam 1'-hydroxylation activity of each cell line with and without $1\alpha,25\text{-}(OH)_2\text{-}D_3$ treatment correlated quite closely with the level of CYP3A immunoreactive protein ($p=0.0003$, $R=0.987$). There was little variability of NADPH cytochrome P450 reductase expression among the clones and parent cell line when untreated, but there was variable responsiveness to $1\alpha,25\text{-}(OH)_2\text{-}D_3$; clone 7 had a response similar to that of the parent cell line but greater than that of the clone 5 (FIG. 7; bottom panel). There was considerable variability among the clones with respect to levels of expression of immunoreactive LFABP, clone 7 being a relatively high expressor (not shown). There was slight variability of P-glycoprotein and villin expression among the clones, clone 7 being a relatively high expressor of both immunoreactive proteins (FIG. 7; bottom panel). Levels of expression of CYP3A5 (FIG. 7; bottom panel) and cytochrome $b_5$, CYP1A1, CYP2D6, and IFABP (not shown) immunoreactive proteins were similar among the clones and the parent cell line.

Therefore, while certain clones exhibited demonstrably enhanced CYP3A4 expression and catalytic activity, measurable CYP3A4 catalytic activity was observed with each of the clones. As such, clonal instability should not be a major concern as long as it is monitored.

EXAMPLE 13

Effects Of Extracellular Matrices On The Increase In CYP3A In Response To $1\alpha,25\text{-}(OH)_2\text{-}D_3$ The experiments of this example demonstrate the effects of several different extracellular matrices on the increase in CYP3A in clone 7 in response to $1\alpha,25\text{-}(OH)_2\text{-}D_3$.

Figure 8B:
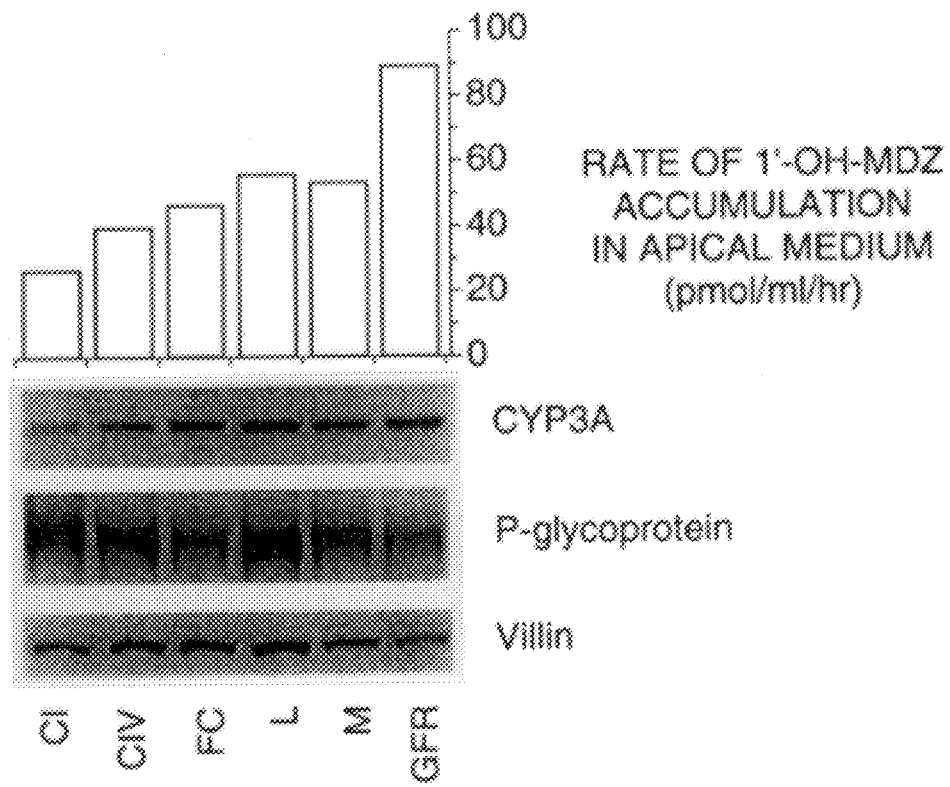
FIG. 8B is a comparison of CYP3A catalytic activity (top panel) and CYP3A expression (immunoblots in bottom panel) for several extracellular matrices in cell cultures treated with $1\alpha,25\text{-(OH)}_2\text{-}D_3$.
Figure 8C:
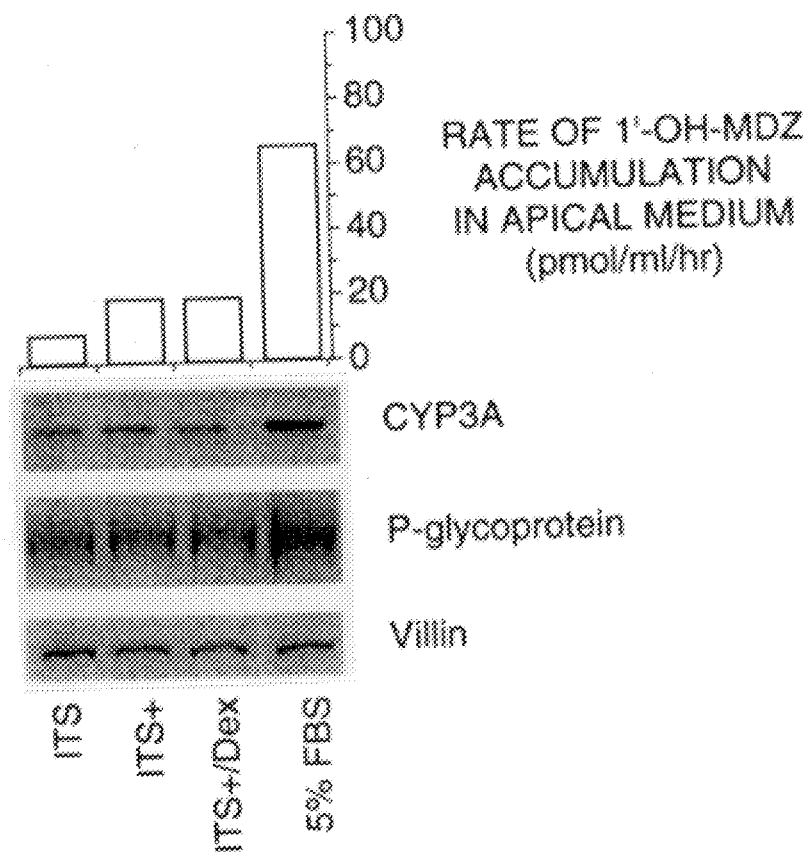
FIG. 8C is a comparison of CYP3A catalytic activity (top panel) and CYP3A expression (immunoblots in bottom panel) in the presence or absence of FBS in cell cultures treated with $1\alpha,25\text{-(OH)}_2\text{-}D_3$.

Caco-2 cells were grown on the various culture inserts indicated below. In each of the experiments, $1\alpha,25\text{-}(OH)_2\text{-}D_3$, if present, was removed at two weeks post-confluence, and the cells were incubated with 4 µM MDZ added to the apical medium. Following incubations of 4.25 to 7 hours (uniform duration within each group), the apical and basolateral media were collected. The rates of 1'-OH-MDZ accumulation in the apical medium are shown in the upper panel of FIGS. 8A–C (ND, not done). The immunoblots shown in the lower panel of FIGS. 8A–C are of 5 µg loads of cell homogenates developed with antibodies of the indicated specificities. Catalytic activity and levels of protein expression were determined as previously described.

Contribution of Matrigel

FIG. 8A indicates the effect of Matrigel (225 µg/cm²). Specifically, Caco-2 cells were grown on polycarbonate culture inserts with (M+) or without Matrigel (M−). Selected cultures were treated (D+) with 0.25 µM $1\alpha,25\text{-}(OH)_2\text{-}D_3$ for two weeks beginning at the time of confluence, while duplicate cultures were left untreated (D−). It should be noted that, in the case of P-glycoprotein, the first pair of lanes is from a different gel than the second pair of lanes, and therefore direct comparisons can only be made within each pair and not between the pairs of immunoreactive bands.

Matrigel alone did not result in increased expression of CYP3A immunoreactive protein (FIG. 8A; M+, D−). Nevertheless, while $1\alpha,25\text{-}(OH)_2\text{-}D_3$ resulted in increased CYP3A protein and catalytic activity in the absence of Matrigel (FIG. 8A; M−, D+), the increase in CYP3A expression in response to $1\alpha,25\text{-}(OH)_2\text{-}D_3$ was clearly enhanced when the Caco-2 cells were grown on Matrigel (FIG. 8A; M+, D+). The rate of 1'-OH-MDZ formation by Caco-2 cells grown on uncoated culture inserts and treated with 0.25 µM $1\alpha,25\text{-}(OH)_2\text{-}D_3$ (FIG. 8A, M−, D+) was only 17% of that of treated cells grown on Matrigel (225 µg/cm²) coated inserts (FIG. 8A; M+, D+).

Comparison of Extracellular Matrices

FIG. 8B compares the effect of several different extracellular matrices. Specifically, Caco-2 cells were grown on polyethylene terephthalate culture inserts commercially coated with the following different extracellular matrices: CI, unpolymerized collagen type I; FC, fibrillar collagen (polymerized type I collagen); CIV, collagen type IV; L, laminin; M, Matrigel; GFR, Growth Factor Reduced Matrigel. The matrix application densities were as previously indicated; the GFR matrix formed a 1–2 mm thick gel. All cultures were treated with 0.25 µM $1\alpha,25\text{-}(OH)_2\text{-}D_3$ for two weeks beginning at the time of confluence.

As the data in FIG. 8B (upper and lower panels) indicate, all extracellular matrices were not equal with respect to expression of CYP3A immunoreactive protein and catalytic activity. Unpolymerized collagen type I was associated with relatively low levels of expression and activity, whereas fibrillar collagen (polymerized type I collagen), laminin, Growth Factor Reduced Matrigel (2.86 mg/cm²), and (to a lesser extent) collagen type IV were associated with levels of expression and activity similar to that seen with Matrigel (2.86 mg/cm²).

It appeared that Caco-2 cell expression of immunoreactive P-glycoprotein, although slightly greater with Matrigel than in the absence of a substratum (FIG. 8A), was greater with single component substrata (collagen type I, collagen type IV, or laminin) than with multicomponent substrata (Matrigel or Growth Factor Reduced Matrigel) (FIG. 8B). Polymerized collagen type I was associated with a level of expression similar to that seen with the multicomponent substrata. These results are similar to those reported for P-glycoprotein expression in cultured rat hepatocytes [J. D. Schuetz and E. G. Schuetz, Cell Growth & Differentiation 4:31–40 (1993)].

A Matrigel substratum appeared to increase the level of immunoreactive villin (FIG. 8A), and the level of villin expression appeared to be similar among cells grown on all of the extracellular matrices examined (FIG. 8B). The histologic appearance by light microscopic examination of H&E stained sections of formalin-fixed and paraffin-embedded monolayers was similar among Caco-2 cells grown on all of the matrices examined (results not shown).

EXAMPLE 14

Effects Of FBS On The Increase In CYP3A In Response To $1\alpha,25\text{-}(OH)_2\text{-}D_3$ Since drugs vary in their degree of protein binding, it would be desirable to be able to eliminate FBS from the medium and manipulate the concentration of albumin or other proteins in a model to study the oral bioavailability of drugs. Elimination of FBS from the system would also make it more defined and reproducible. This example, a continuation of the experiments performed in the preceding example, assesses the effect of FBS on CYP3A expression and catalytic activity.

Responsiveness of CYP3A expression to $1\alpha,25-(OH)_2-D_3$ was compared in Caco-2 cells grown on Matrigel in the presence or absence of 5% FBS for the two week post-confluence period. The serum-free medium was supplemented with ITS# (selenous acid 5 μg/L, insulin and transferrin 5 mg/L final concentrations), ITS+# (selenous acid 6.2 μg/L, insulin and transferrin 6.2 mg/L, bovine serum albumin 1.25 g/L, linoleic acid 5.35 mg/L final concentrations), or ITS+# with 100 nM dexamethasone (Dex).

FIG. 8C compares the contribution of FBS. The level of expression of CYP3A immunoreactive protein (FIG. 8C, lower panel) was similar among the three serum free cultures but was much lower than that achieved with 5% FBS. CYP3A catalytic activity in the serum free cultures was only 30% of that obtained in the presence of 5% FBS (FIG. 8C, upper panel). Immunoreactive P-glycoprotein also appeared to be diminished in the absence of FBS (FIG. 8C) while villin expression appeared to be unaffected. Levels of expression of immunoreactive NADPH cytochrome P450 reductase, cytochrome $b_5$, IFABP, and LFABP also did not appear to be influenced by the removal of serum (not shown). Glucocorticoids, which have been shown to increase the number of vitamin D receptors in rat intestine and in osteoblast-like cells, are unlikely to be a key ingredient in FBS since the addition of 100 nM dexamethasone to the serum free medium did not restore full responsiveness (FIG. 8C).

Though an understanding of the effect of FBS is not required to practice the present invention, it appeared that FBS may have functioned to prevent toxicity by $1\alpha,25-(OH)_2-D_3$ by limiting its free concentration, since at the highest concentrations used, both $1\alpha,25-(OH)_2-D_3$ and $25-(OH)-D_3$ were associated with lower levels of expression of CYP3A4 (see FIGS. 2C and 3) and villin (see FIG. 3). However, results of a subsequent dose-response experiment using $1\alpha,25-(OH)_2-D_3$ under serum-free conditions (not shown) suggested that FBS is providing some essential element to the system or perhaps is preventing toxic effects from some other component of the medium.

EXAMPLE 15

The Effect Of Serum-Free Conditions

Previous examples have described experiments wherein the Caco-2 cells were grown in a medium containing serum. As previously noted, however, the present invention contemplates performing drug metabolism studies in a serum-free medium. This example describes midazolam incubation studies with Caco-2 cells under serum-free conditions.

For the experiments of this example, Caco-2 cells from three different cell cultures were grown on Matrigel-coated teflon culture inserts. Each of the three cultures was treated with 0.25 μM $1\alpha,25-(OH)_2-D_3$ for two weeks beginning at the time of confluence. At the end of this period, the medium was replaced with medium containing neither serum nor vitamin D. Next, MDZ (4 μM) was added to the apical compartment. After 6.5 hours, the luminal and basolateral media were collected separately.

Figure 9:
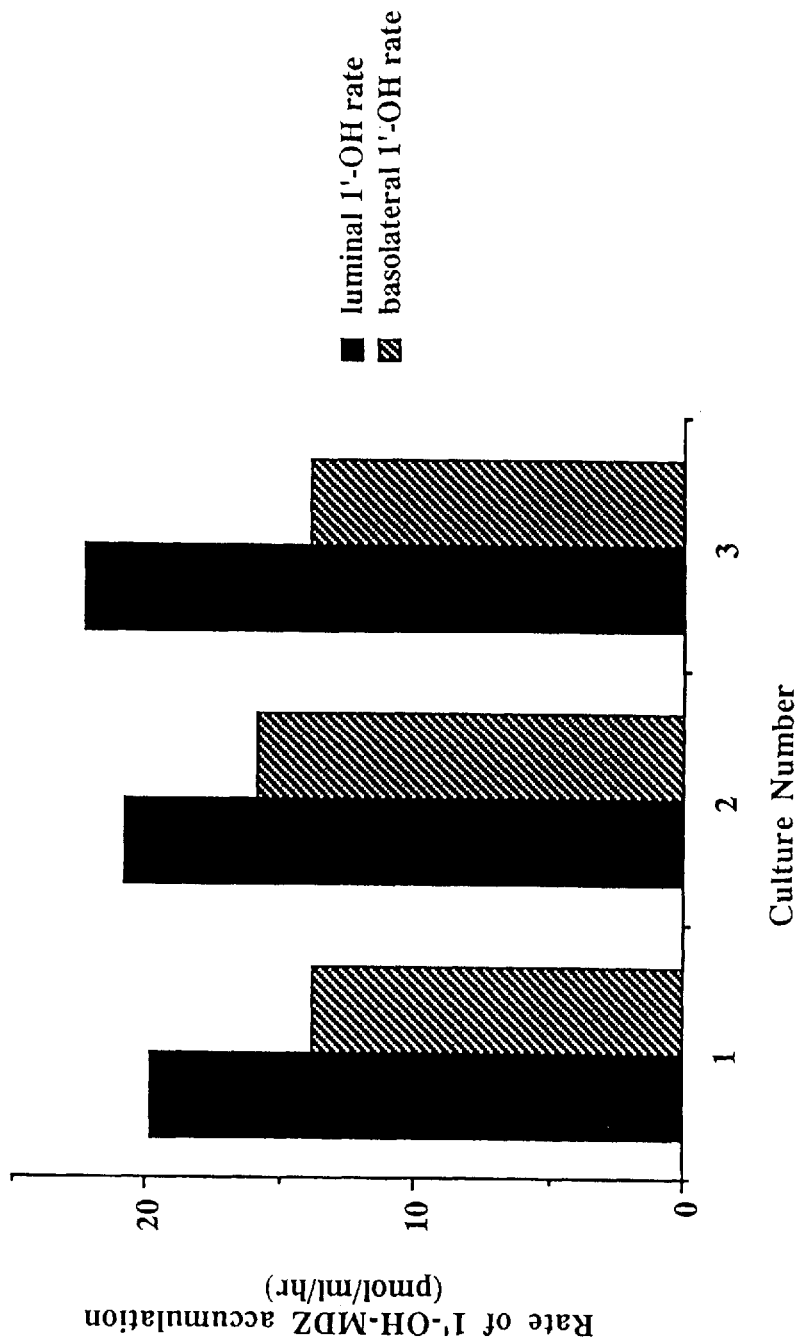
FIG. 9 graphically illustrates CYP3A catalytic activity, as determined by the rate of 1'-OH-MDZ accumulation, in serum-free apical (luminal) and basolateral (serosal) medium.

FIG. 9 graphically illustrates CYP3A catalytic activity, as determined by the rate of 1'-OH-MDZ accumulation, in apical (luminal) and basolateral (serosal) medium. As the data indicate, the rate of 1'-OH-MDZ formation was greater in the luminal medium than in the basolateral medium with all three cultures. Importantly, the rate of 1'-OH-MDZ formation was decreased compared to that measured in the presence of serum. For example, the rate of formation was less than that previously described when cells were grown on Matrigel and treated with 0.25 μM $1\alpha,25-(OH)_2-D_3$ (FIG. 8A; M+, D+), indicating that the presence of serum leads to increased metabolism.

---

We claim:
1. A method of treating cells, comprising the steps of:
   a) providing:
      i) cells responsive to treatment with analogs of vitamin $D_3$,
      ii) an analog of vitamin $D_3$, and
      iii) an extracellular matrix;
   b) plating said cells on said extracellular matrix; and
   c) treating said plated cells with said analog of vitamin $D_3$.
2. The method of claim 1, wherein said treating causes said cells to exhibit enhanced expression of CYP3A4.

3. The method of claim 1, wherein said cells are from a cell line selected from the group consisting of hepatocellular carcinoma cells, colonic adenocarcinoma cells, pancreatic carcinoma cells, pancreatic adenocarcinoma cells, skin cells, and kidney cells.

4. The method of claim 3, wherein said cells are Caco-2 cells.

5. The method of claim 1, further comprising, prior to step b), seeding said cells onto a cell support matrix.

6. The method of claim 5, wherein said cell support matrix is a culture insert.

7. The method of claim 6, wherein said culture insert is permeable.

8. The method of claim 1, wherein said analog of vitamin $D_3$ is selected from the group consisting of 1α,25-dihydroxyvitamin $D_3$ and 25-hydroxyvitamin $D_3$.

9. The method of claim 1, wherein said extracellular matrix is selected from the group consisting of unpolymerized collagen type I, polymerized collagen type I, collagen type IV, laminin, Matrigel, and Growth Factor Reduced Matrigel.

10. The method of claim 1, wherein said cells are grown in the presence of serum.

11. A cell line with enhanced expression of a member of the CYP3A subfamily made by the process of:
    a) providing:
        i) Caco-2 cells,
        ii) an analog of vitamin $D_3$, and
        iii) an extracellular matrix;
    b) plating said Caco-2 cells on said extracellular matrix;
    c) treating said plated Caco-2 cells with said analog of vitamin $D_3$; and
    d) isolating those treated cells that exhibit enhanced expression of a member of the CYP3A subfamily.

12. The cell line of claim 11, wherein said member comprises CYP3A4.

13. The cell line of claim 11, further comprising, prior to step b), seeding said Caco-2 cells onto a cell support matrix.

14. The cell line of claim 13, wherein said cell support matrix is a culture insert.

15. The cell line of claim 14, wherein said culture insert is permeable.

16. The cell line of claim 11, wherein said analog of vitamin $D_3$ is selected from the group consisting of 1α,25-dihydroxyvitamin $D_3$ and 25-hydroxyvitamin $D_3$.

17. The cell line of claim 11, wherein said extracellular matrix is selected from the group consisting of unpolymerized collagen type I, polymerized collagen type I, collagen type IV, laminin, Matrigel, and Growth Factor Reduced Matrigel.

18. The cell line of claim 11, wherein said treating comprises exposing said Caco-2 cells to said vitamin $D_3$ analog for approximately two weeks beginning at the time of confluence.

19. The cell line of claim 18, wherein said Caco-2 cells are grown in the presence of serum.

20. A system for screening the bioavailability of compounds, comprising gastrointestinally-derived cells exhibiting enhanced expression of CYP3A4 seeded onto a cell support matrix.

21. The system of claim 20, wherein said cell support matrix is a culture insert.

22. The system of claim 21, wherein said culture insert is permeable.

23. The system of claim 20, wherein said enhanced expression by said cells results from exposing said cells to an analog of vitamin $D_3$.

24. The system of claim 23, wherein said analog of vitamin $D_3$ is selected from the group consisting of 1α,25-dihydroxyvitamin $D_3$ and 25-hydroxyvitamin $D_3$.

25. The system of claim 23, wherein said cells are grown in the presence of serum.

26. The system of claim 20, wherein said gastrointestinally-derived cells are from a cell line selected from the group consisting of colonic adenocarcinoma cells, stomach adenocarcinoma cells, and stomach carcinoma cells.

27. The system of claim 26, wherein said colonic adenocarcinoma cells are Caco-2 cells.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGCTATCACA  GATCCTGACA  TGATCAAACT                                    3 0

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TGTGGGACTC AGTTTCTTTT GAATTCTTAT 30

( 2 ) INFORMATION FOR SEQ ID NO:3:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:3:

TGGACCCAGA AACTGCATTG GCATGAGGTT 30

( 2 ) INFORMATION FOR SEQ ID NO:4:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:4:

ACTCTACACA GACAATGAGA GAGCTCCGGA 30

( 2 ) INFORMATION FOR SEQ ID NO:5:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:5:

CATTGGATGA AGCCATCTCA TTTCAGAGTC 30

( 2 ) INFORMATION FOR SEQ ID NO:6:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:6:

CCTTACACAT ACACACCCTT TGGAAGT 27

( 2 ) INFORMATION FOR SEQ ID NO:7:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:7:

AGCTCAATGC ATGTACAGAA TCCCCGGTTA 30

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CCCAGTTGCT ATTAGACTTG A 21

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TTCTGGTTGA AGAAGTCCTT GCGTGTC 27

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AGTATAGAAA AGTCTGGGGT ATTTATGACT 30

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TATTGAGAGA ACGAATGGAT CTAATGG 27

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GTCATTGTGG AGAAAGGAAA TCATG 25

( 2 ) INFORMATION FOR SEQ ID NO:13:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:13:

ATTCCAAGGG CTAGAAACAA TAGTG 25

( 2 ) INFORMATION FOR SEQ ID NO:14:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

AGGAAGCTTG CAGCTCATGA CAATTTGAAG 30

( 2 ) INFORMATION FOR SEQ ID NO:15:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

AGTATTCAGT TCGTTTCCAT TGTCTGTCCG 30

( 2 ) INFORMATION FOR SEQ ID NO:16:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:16:

CAGCTAGTGA ACAAGCCTGT AGAGGAGCTC 30

( 2 ) INFORMATION FOR SEQ ID NO:17:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:17:

GCCACAGAAG TTTGTGCTCA TAGGCACATC 30